United States Patent [19]
Nishiyama et al.

[11] Patent Number: 5,929,284
[45] Date of Patent: Jul. 27, 1999

[54] PROCESSES FOR PRODUCING α-HALO KETONES, α-HALOHYDRINS AND EPOXIDES

[75] Inventors: Akira Nishiyama, Kobe; Tadashi Sugawa, Akashi; Hajime Manabe, Takasago; Kenji Inoue, Kakogawa; Noritaka Yoshida, Matsubara, all of Japan

[73] Assignee: Kaneka Corporation, Osaka, Japan

[21] Appl. No.: 08/722,102

[22] PCT Filed: Feb. 2, 1996

[86] PCT No.: PCT/JP96/00212

§ 371 Date: Dec. 18, 1996

§ 102(e) Date: Dec. 18, 1996

[87] PCT Pub. No.: WO96/23756

PCT Pub. Date: Aug. 8, 1996

[30] Foreign Application Priority Data

Feb. 3, 1995 [JP] Japan .................................. 7-039266
Sep. 26, 1995 [JP] Japan .................................. 7-273547

[51] Int. Cl.[6] .................................................. C07C 45/00
[52] U.S. Cl. ...................... 568/319; 549/520; 568/306; 568/307; 568/397; 568/713; 568/814; 568/841; 568/842
[58] Field of Search ............................. 549/520; 568/306, 568/307, 319, 397, 713, 814, 841, 842

[56] References Cited

U.S. PATENT DOCUMENTS

| | | | |
|---|---|---|---|
| 5,475,136 | 12/1995 | Fritz et al. ................................ | 564/162 |
| 5,481,011 | 1/1996 | Chen et al. ............................... | 549/514 |
| 5,495,054 | 2/1996 | Goa et al. ................................. | 568/799 |
| 5,523,463 | 6/1996 | Hilpert ..................................... | 560/137 |
| 5,591,885 | 1/1997 | Hilpert ..................................... | 560/29 |
| 5,684,176 | 11/1997 | Hilpert ..................................... | 560/29 |
| 5,693,847 | 12/1997 | Tung et al. ............................... | 560/16 |

FOREIGN PATENT DOCUMENTS

| | | | |
|---|---|---|---|
| 0 580 402 A2 | 1/1994 | European Pat. Off. ...... | C07C 271/20 |
| 0 604 185 A1 | 6/1994 | European Pat. Off. ...... | C07D 217/26 |

OTHER PUBLICATIONS

CA 106:2196, corresponding to Rauber et al., Biochem J., vol. 239(3), pp. 633–640, 1986.

Tanabe, "The Selective Claisen and Dieckmann Ester Condensations Promoted by Dichlorobis(trifluoromethanesulfonato) titanium(IV)", Bull.Chem.Soc.Jpn., vol. 62, pp. 1917–1924, 1989.

Barluenga et al. "The First Direct Preparation of Chiral Functionalised Ketones and their Synthetic Uses", J.Chem.Soc.,Chem.Comm., pp. 969–970, 1994.

McMurry, "Organic Chemistry", p. 629, 1988.

Albeck et al. "Stereocontrolled Synthesis of Erythro N–Protected alpha–Amino Epoxides and Peptidyl Epoxides", Tetrahedron, vol. 50(21), pp. 6333–6346, 1994.

*Primary Examiner*—John Kight
*Assistant Examiner*—Garth M. Dahlen
*Attorney, Agent, or Firm*—Pollock, Vande Sande & Priddy

[57] ABSTRACT

Processes for efficiently producing α-halo ketones, α-halohydrins and epoxides on an industrial scale. The prosesses include one for producing an α-halo ketone of general formula (3) by decarboxylating a product of reaction between a carboxylic acid derivative of general formula (1) and a metal enolate prepared from an α-haloacetic acid of general formula (2) or an acceptable salt thereof, one for producing an by reducing the α-halo ketone (3), and one for producing an epoxide (13) by treating the α-halohydrin (11) with a base to effect ring closure. The above prosesses are particularly suitable for producing optically active α-halo ketones, α-halohydrins and epoxides from the corresponding α-amino acid derivatives.

$R^1COA$ (1)

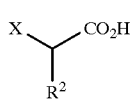

(2)

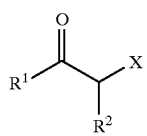

(3)

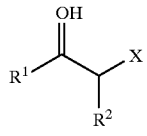

(11)

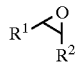

(13)

53 Claims, 18 Drawing Sheets

PROCESSES FOR PRODUCING α-HALO KETONES, α-HALOHYDRINS AND EPOXIDES

This application in a 371 of PCT/JP96/00212 filed Feb. 2, 1996.

TECHNICAL FIELD

The present invention relates to a process for producing an α-halo ketone from a carboxylic acid derivative or ester utilizing an α-haloacetic acid, a process for producing an α-halohydrin by reducing the α-halo ketone so produced, and a process for producing an epoxide by reducing the α-halohydrin so produced.

More particularly, the present invention relates to a technology for producing aminohalo ketones, aminohalohydrins and aminoepoxides from amino acid derivatives or amino acid esters and particulary to a technology for producing optically active α-halo ketones, α-halohydrins and epoxides from the corresponding optically active amino-protected phenylalanine esters. α-Halo ketones, α-halohydrins and epoxides originating from optically active phenylalanine are compounds of value as intermediates for the production of medicines.

BACKGROUND TECHNOLOGY

The following processes are known for the production of aminohalo ketones.

(1) A process for producing a chloroketone or an aminochloroketone which comprises converting an amino-protected amino acid to a mixed acid anhydride, reacting the anhydride with diazomethane to give an amino diazoketone and treating the ketone with hydrochloric acid (Siegfried Fittkau et al., Journal fur Praktische Chemie, 529, 1986).

(2) A process for producing an aminochloroketone which comprises converting an amino-protected amino acid to a mixed acid anhydride, reacting the anhydride with diazomethane to give an aminodiazoketone, and treating the ketone with a metal chloride (Japanese Kokai Publication Hei-5-117169).

(3) A process for producing a chloroketone or an aminochloroketone which comprises reacting an amino-protected amino acid ester with a halomethyllithium (J. Chem. Soc. Chem. Commun., 969, 1994).

As the production technology for aminohalohydrins and aminoepoxides, the following processes are known.

(4) A process comprising reducing an α-chloroketone as typically obtained by the above process (1) or (2) to a α-halohydrin using a reducing agent such as sodium borohydride and a process comprising treating said α-halohydrin further with a base to give the corresponding epoxide (Tetrahedron, 50, 6333, 1994; J. Medic. Chem., 37, 1738, 1994; J. Medic. Chem., 34, 1221, 1991).

(5) A process comprising permitting sulfoniumylide to act on an amino-protected aminoaldehyde to give an epoxide (Tetrahedron Lett., 30, 3425, 1989; J. Org. Chem., 50, 4615, 1985).

(6) A process comprising permitting a peracid to act on an amino-protected allylamine derivative to synthesize an epoxide (Tetrahedron Lett., 35, 4939, 1994).

(7) A process comprising permitting a halomethyllithium to act on an amino-protected α-aminoaldehyde to produce an aminoepoxide (WO 93/23388).

Processes (1) and (2), wherein the explosive diazomethane is employed, are not satisfactory as industrial processes. Process (3) can hardly be implemented on an industrial scale partly because a low reaction temperature not exceeding −70° C. is essential and partly because it is applicable only to special cases using dibenzyl group as an amino-protecting group.

Further, process (4) comprising reducing chloroketones to chlorohydrins is not flawless in industrial applicability because there is no established industrial production technology for chloroketones. Processes (5), (6) and (7) for the production of epoxides are disadvantageous in that epoxides of the threo configuration are preferentially produced, with the erythro-epoxides being not obtainable unless special amino-protecting groups are employed.

SUMMARY OF THE INVENTION

Under the above circumstances the present invention provides processes for efficiently producing α-haloketones, α-halohydrins and epoxides on an industrial scale.

With the thought that establishing an efficient industrial process for converting a carboxylic acid derivative to an α-chloroketone should lead to the ultimate establishment of processes for efficiently producing the corresponding chlorohydrin and epoxide on an industrial scale, the inventors of the present invention did much research and found that by reacting a metal enolate prepared from an α-haloacetic acid or an acceptable salt thereof with a carboxylic acid derivative, particularly a carboxylic acid ester, the objective α-halo ketone can be obtained in safety in a single step through in situ decarboxylation. They further discovered that this process can be successfully exploited for the conversion of optically active α-amino acid derivatives, particularly optically active α-amino acid esters, to the corresponding optically active α-halo ketones.

The inventors further developed processes for producing optically active halohydrins and epoxides in 2 or 3 steps from α-amino derivatives, particularly α-amino acid ester derivatives, by reducing said α-halo ketones to α-halohydrins and further to epoxides. The present invention has been developed on the basis of the above findings.

Therefore, the present invention is directed to a process for producing an α-halo ketone of general formula (3)

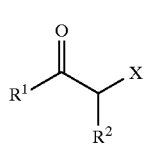
(3)

(wherein $R^1$ represents alkyl, aralkyl or aryl; $R^2$ represents hydrogen, alkyl, aralkyl or aryl; X represents halogen) which comprises reacting a carboxylic acid derivative of the general formula (1)

$$R^1COA \qquad (1)$$

(wherein $R^1$ are as defined above; A represents a leaving group), or a carboxylic acid ester of the general formula (4)

$$R^1CO_2R^3 \qquad (4)$$

(wherein $R^1$ and $R^3$ independently represent alkyl, aralkyl or aryl) with a metal enolate prepared from an α-haloacetic acid of the general formula (2)

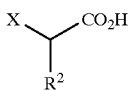

(2)

(wherein R² and X are as defined above) R² represents hydrogen, alkyl, aralkyl or aryl; X represents halogen) or an acceptable salt thereof and decarboxylating the reaction product in situ;

a process for producing an α-halohydrin of the general formula (11)

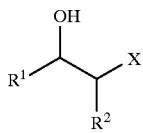

(11)

(wherein R¹, R² and X are as defined above) which comprises reducing said α-halo ketone;

a process for producing an epoxide of the general formula (13)

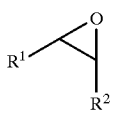

(13)

(wherein R¹ and R² are as defined above) which comprises treating said α-halohydrin with a base;

and processes for producing a chloroketone (9), a chlorohydrin (12) and an epoxide (14) which comprises using an amino acid ester of the general formula (8)

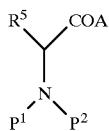

(8)

(wherein R⁵ represents hydrogen, alkyl, aralkyl or aryl; A represents a leaving group; P¹ and P² independently represent hydrogen or an amino-protecting group or, taken together, represent phthaloyl), or of the general formula (10)

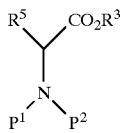

(10)

(wherein R³ represents alkyl, aralkyl or aryl; R⁵ represents hydrogen, alkyl, aralkyl or aryl; P¹ and P² independently represent hydrogen or an amino-protecting group or, taken together, represent phthaloyl), and particularly a process for producing the corresponding optically active chloroketone, chlorohydrin and epoxide which comprises using an optically active L-phenylalanine ester or D-phenylalanine ester.

DESCRIPTION OF THE INVENTION

Figure 1:
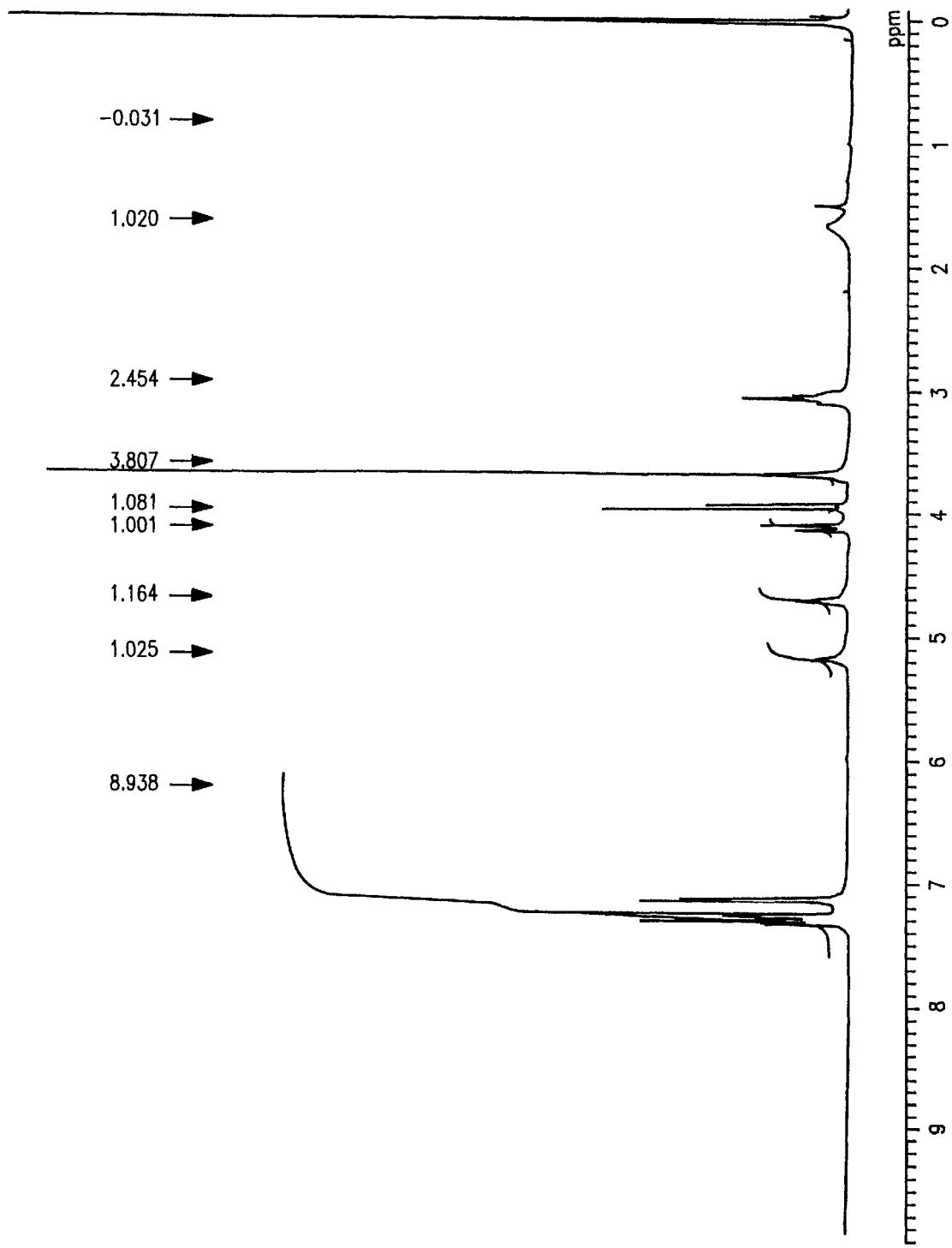
FIG. 1 shows an NMR chart of L-[N-(methoxycarbonyl) phenylalanyl]methyl chloride (II) as obtained in Example 10.

Taking an exemplary combination of substrates and reactants falling under the purview of the present invention, the reaction scheme of the invention is presented below.

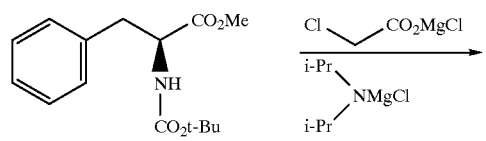

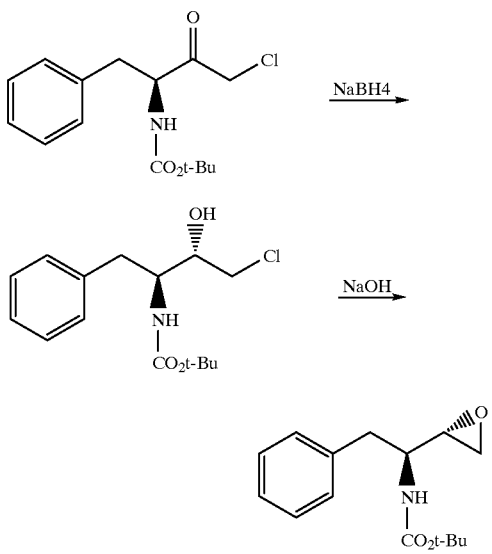

The α-halohydrins and epoxides originating from L-phenylalanine, which are obtainable with advantage in accordance with the production technology of the present invention, can for example be derivatized to HIV protease inhibitors as reported by Kevin E. B. Parkes et al. (J. Org. Chem., 59, 3656, 1994).

The present invention is now described in detail.

A, referred to hereinbefore, is a group known to be capable of leaving and also forming a reactive carboxylic acid derivative in the form of COA, thus including but being not limited to alkoxy groups such as methoxy, ethoxy, etc., alkoxycarbonyl groups such as methoxycarbonyl, ethoxycarbonyl, etc., groups forming metal salts of carboxylic acids, such as OLi, ONa, etc., and halogen atoms such as Cl, Br and the like.

$R^1$, referred to hereinbefore, represents, each as optionally substituted, straight-chain or branched alkyl of 1 to 30 carbon atoms, aryl of 6 to 35 carbon atoms, or aralkyl of 7 to 36 carbon atoms, thus including but being not limited to $CH_3$—, $CH_3(CH_2)n$— (where n represents an integer of 1 to 29), $(CH_3)_2$—CH—, $(CH_3)_3C(CH_2)$—, $(CH_3)_2CH(CH_2)_2$—, Ph— (where Ph represents phenyl), and $Ph(CH_2)m$— (where m represents an integer of 1 to 9).

$R^2$, referred to hereinbefore, represents hydrogen, alkyl of 1 to 5 carbon atoms, aryl of 6 to 10 carbon atoms, or aralkyl of 7 to 11 carbon atoms, and is preferably hydrogen.

$R^3$, referred to hereinbefore, represents, each as optionally substituted, straight-chain or branched alkyl of 1 to 10 carbon atoms, aryl of 6 to 15 carbon atoms, or aralkyl of 7 to 21 carbon atoms, thus including but being not limited to methyl, ethyl, n-propyl, isopropyl, n-butyl, phenyl, benzyl, α-methylbenzyl, and phenylpropyl. Particularly preferred are methyl and ethyl.

A preferred example of the metal enolate mentioned above is a magnesium enolate prepared by reacting a magnesium amide of the general formula (5)

(5)

(wherein B and D independently represents alkyl, aralkyl, aryl or silyl or, taken together, represent cycloalkyl; Y represents

or halogen) with an α-haloacetic acid of the general formula (2) or an acceptable salt thereof; and a magnesium enolate prepared by reacting a Grignard reagent of the general formula (6)

 $R^4MgZ$ (16)

(wherein $R^4$ represents alkyl, aralkyl, or aryl; Z represents halogen or $R^4$) and an α-haloacetic acid of the general formula (2) or an acceptable salt thereof.

In the specification of the present invention, the terms "metal enolate", "enolate" and "enolate anion" mean the anionic active species formed by the reaction between an α-haloacetic acid such as monochloroacetic acid or a salt thereof and a base such as chloromagnesium diisopropylamide. The term "Mg enolate" means the anionic active species formed by the reaction between an α-haloacetic acid or a salt thereof and an Mg base such as chloromagnesium diisopropylamide or t-butylmagnesiumamide.

B and D, referred to above, independently represent straight-chain or branched alkyl of 1 to 10 carbon atoms, aryl of 6 to 15 carbon atoms, aralkyl of 7 to 21 carbon atoms, or silyl of 3 to 10 carbon atoms, thus including but being not limited to isopropyl, methyl, ethyl, phenyl, benzyl, trimethylsilyl, and, taken together, cyclohexyl. Particularly preferred are cases in which both B and D represent isopropyl, both B and D represent trimethylsilyl, and B and D, taken together, represent cyclohexyl.

$R^4$, referred to above, represents straight-chain or branched alkyl of 1 to 10 carbon atoms, aryl of 6 to 15 carbon atoms, or aralkyl of 7 to 21 carbon atoms, including but being not limited to t-butyl, t-amyl, isopropyl, sec-butyl, methyl, ethyl, benzyl, and phenyl. Particularly preferred are quaternary or tertiary alkyl groups such as t-butyl, t-amyl, isopropyl, and sec-butyl.

$R^5$, referred to above, represents hydrogen or, each as optionally substituted by a hetero-atom, straight-chain or branched alkyl of 1 to 20 carbon atoms, aryl of 6 to 25 carbon atoms, or aralkyl of 7 to 26 carbon atoms, and is typically the side chain of a common amino acid or the side chain of an amino acid derivative obtained by modifying a common amino acid.

Specifically, methyl, ethyl, isopropyl, t-butyl, hydroxymethyl, 1-hydroxyethyl, mercaptomethyl, methylthiomethyl, phenylthiomethyl, phenyl, p-methoxyphenyl, p-hydroxyphenyl, benzyl, p-methoxybenzyl, etc. can be mentioned.

$P^1$ and $P^2$, both referred to above, independently represent hydrogen or an amino-protecting group. The amino-protecting group is not particularly limited but can be any protecting group that is conventionally used for masking an amino group, thus including the species described in inter alia Protective Groups in Organic Synthesis, 2nd Ed. (authored by Theodora W. Green and published by John Wiley & Sons, 1990) on pages 309 to 384. Thus, methoxycarbonyl, t-butoxycarbonyl, benzyloxycarbonyl, ethoxycarbonyl, acetyl, trifluoroacetyl, benzyl, dibenzyl, phthalimido, tosyl, benzoyl, etc. can be mentioned. Particularly preferred are methoxycarbonyl, t-butoxycarbonyl, ethoxycarbonyl, benzyloxycarbonyl and dibenzyl. When $P^1$ and $P^2$, mentioned above, jointly represent a phthaloyl group, it can be regarded as a form of said amino-protecting group.

X represents halogen and specifically includes Cl, Br, I, and F. Particularly preferred is Cl. Y, Z and W each may represent halogen, in which case it can be Cl, Br, I or F.

The acceptable salt of α-haloacetic acid mentioned above includes the sodium salt, magnesium salt, lithium salt, potassium salt, zinc salt, calcium salt, copper salt, trimethylsilyl salt, ammonium salt, etc. These salts may be prepared in the reaction system for use as they are or be previously prepared.

As specific examples of said α-haloacetic acid of general formula (2) or of said acceptable salt thereof there can be mentioned monochloroacetic acid, monobromoacetic acid, monofluoroacetic acid, sodium monochloroacetate, chloromagnesium monochloroacetate, bromomagnesium monochloroacetate, magnesium bis(monochloroacetate , lithium monochloroacetate, potassium monochloroacetate, trimethylsilyl monochloroacetate, monochloropropionic acid and so forth.

Moreover, a variety of ammonium salts of monochloroacetic acid with ammonia, t-butylamine, diethylamine, diisopropylamine, triethylamine, diisopropylethylamine, pyridine, 2,6-lutidine, N,N-dimethylaniline, N-ethylpiperidine, N-methylmorpholine, diazabicyclotriethylenediamine, etc. can also be mentioned. While ammonium salts can be mentioned but not limited to the above, the ammonium salts with secondary or tertiary amines are preferred.

The conditions for practicing the processes for producing in the present invention are now described.

Regarding the production method for a salt of the α-haloacetic acid of general formula (2), various processes can be mentioned according to the kinds of salt-forming metals. For example, by treating sodium monochloroacetate with a metal salt such as magnesium chloride, calcium chloride, zinc chloride or aluminum chloride in a suitable solvent, the corresponding metal salt can be obtained. Moreover, by treating an α-haloacetic acid such as monochloroacetic acid with said amines, respectively, in a suitable solvent, a variety of ammonium salts can be obtained.

Taking the production of magnesium monochloroacetate as an example, the following processes can be mentioned.

① A process in which sodium monochloroacetate is treated with preferably 1 to 2 molar equivalents, based on sodium monochloroacetate, of an inorganic magnesium salt such as magnesium chloride, magnesium sulfate or the like in a solvent such as tetrahydrofuran (THF), t-butyl methyl ether (MTBE) or the like and the reaction mixture is used as it is or after the byproduct sodium salt such as sodium chloride is filtered off.

② A process in which monochloroacetic acid is either treated with preferably 1 to 2 molar equivalents, based on the same acid, of magnesium in a solvent such as THF, MTBE or the like and the resulting magnesium monochloroacetate is used as it is or treated with preferably 1 to 2 molar equivalents, based on the same acid, of an inorganic magnesium salt such as magnesium chloride, magnesium sulfate or the like and the resulting product such as chloromagnesium monochloroacetate is used.

The metal enolate mentioned above is produced by treating a haloacetic acid with 2 or more molar equivalents of a base or treating a previously prepared acceptable salt of the α-haloacetic acid with a base.

The base that can be used for this purpose includes magnesium amides such as chloromagnesium diisopropylamide, bromomagnesium diisopropylamide, magnesium bis(diisopropyl)amide, chloromagnesium dicyclohexylamide, chloromagnesium t-butylamide, chloromagnesium hexamethyldisilazide, etc.; alkylmagnesium compounds such as t-butylmagnesium chloride, t-butylmagnesium bromide, t-amylmagnesium chloride, di-t-butylmagnesium, isopropylaminomagnesium chloride, etc.; organolithium compounds such as lithium diisopropylamide, lithium hexamethyldisilazide, lithium cyclohexylamide, n-butyl lithium, t-butyllithium, etc.; potassium t-butoxide, sodium hydride, magnesium ethoxide, sodium ethoxide, and so forth. Particularly preferred are magnesium amides such as chloromagnesium diisopropylamide etc. and quarternary alkylmagnesium compounds such as t-butylmagnesium chloride and so forth. These substances can be used singly or in combination.

The amount of said base, in case said acceptable salt of α-haloacetic acid is prepared in situ, is 2 to 6 molar equivalents, preferably 2 to 3 molar equivalents, based on the α-haloacetic acid. Where said acceptable salt of α-haloacetic acid is prepared beforehand, the base is used in a proportion of 1 to 3 molar equivalents, preferably 1 to 1.5 molar equivalents, based on the α-haloacetic acid.

When a Grignard reagent such as t-butylmagnesium chloride is used for the base, an enhanced yield can be expected by adding amine independently. The amine that can be used for this purpose is usually a secondary amine or a tertiary amine, and is preferably a tertiary amine. Thus, the amine includes but is not limited to diisopropylamine, triethylamine, diisopropylethylamine, pyridine, 2,6-lutidine, N,N-dimethylaniline, N-ethylpiperidine, N-methylmorpholine, and diazabicyclotriethylenediamine. There is no particular limitation on the amount of the amine but the amine is used in a proportion of preferably 0.01 to 10 molar equivalents and more preferably 0.1 to 6 molar equivalents based on the carboxylic acid derivative of general formula (1) or (8), particularly the ester of general formula (4) or (10). These amines can be added previously to the reaction system or added with the progress of reaction.

The reaction solvent that can be used includes tetrahydrofuran, t-butyl methyl ether, diethyl ether, 1,2-dimethoxyethane, N,N-dimethylformamide, N-methylpyrrolidone, 1,3-dimethyl-2-imidazolidinone, and toluene, among others. These solvents are used singly or in combination.

The enolate of the salt of a haloacetic acid can be prepared by treating the α-haloacetic acid or a salt thereof with above-mentioned molar equivalent of said base in said solvent at −70° C. to 40° C., preferably −30° C. to 20° C., and more preferably −30° C. to 0° C. and stirring the mixture for 10 minutes to 20 hours, preferably 30 minutes to 5 hours.

The α-haloacetate enolate anion of the salt of an α-haloacetic acid generated in this manner is allowed to react with a carboxylic acid derivative of general formula (1) or (8), particularly an ester of general formula (4) or (10) to give the objective α-halo ketone through decarboxylation in situ. The term in situ means any stage of the course from the beginning of mixing of the reactants to the end of after-treatment. The proportion of the α-haloacetic acid or salt thereof to the carboxylic acid derivative or ester is 1 to 4 equivalents, preferably 1 to 3 equivalents.

As to the reaction procedure, the above reaction can be carried out typically by adding said carboxylic acid derivative or ester or a solution thereof in a reaction solvent to the enolate anion solution prepared as above at −70° C. to 40° C., preferably −50° C. to 30° C., more preferably −30° C. to 20° C. and stirring the mixture for 10 minutes to 20 hours, preferably 30 minutes to 10 hours.

It is also possible to add the enolate anion of the α-haloacetate to the carboxylic acid derivative or ester and stir the mixture under the like conditions or, as a further alternative, it is possible to react the haloacetic acid or a salt thereof with said base in the presence of the carboxylic acid derivative or ester and allow the resulting enolate anion of the α-haloacetate to take part in the reaction.

Among species of the N-protected amino acid derivative of general formula (8) or of the N-protected amino acid ester of general formula (10), regarding any compound having hydrogen bound to N, N atom can be previously protected with e.g. a trimethylsilyl group by reacting the substrate compound with a silylating agent, e.g. trimethylsilyl chloride, in the presence of a base, or submitted to the reaction without prior protection. When it is to be protected, the reaction solvent mentioned above can be used as the solvent.

The after-treatment following the reaction may typically comprise the following procedure. After the above reaction time, the reaction is stopped by adding diluted hydrochloric acid, an aqueous solution of ammonium chloride, or the like and the reaction mixture is extracted with a solvent such as ethyl acetate, diethyl ether, toluene or the like. The extract is washed with saturated NaHCO$_3$ solution, saturated NaCl solution, etc. and dehydrated over a desiccant such as anhydrous sodium sulfate or magnesium sulfate. After the desiccant is filtered off, the filtrate is concentrated and purified by conventional means known to those skilled in the art, such as recrystallization or column chromatography, to provide the α-halo ketone of general formula (3) or general formula (9).

This α-halo ketone of general formula (3) or general formula (9) is then reduced to the α-halohydrin of general formula (11) or general formula (12). This step is now described.

This reduction can be carried out typically under the conditions described in Journal of Medicinal Chemistry, 37, 1738, 1994. As the reducing agent, sodium borohydride can be used with advantage. Its amount is 1 to 10 molar equivalents, preferably 2 to 3 molar equivalents, based on the α-halo ketone.

The reaction solvent that can be used includes lower alcohols such as methanol, ethanol, etc., water, toluene, ethyl acetate, and tetrahydrofuran, among others. These solvents can be used singly or as a mixture.

The reaction is carried out under stirring at −10° C. to 40° C., preferably −10° C. to 10° C., for 10 to 20 minutes, preferably 30 to 60 minutes.

The after-treatment following the reaction may typically comprise the following procedure. After the above reaction time, the reaction is stopped by adding diluted hydrochloric acid, an aqueous solution of ammonium chloride, or the like and the reaction mixture is extracted with a solvent such as ethyl acetate, diethyl ether, toluene or the like. The extract is washed with saturated NaHCO$_3$ solution, saturated NaCl solution, etc. and dehydrated over a desiccant such as anhydrous sodium sulfate or magnesium sulfate, After the desiccant is filtered off, the filtrate is concentrated and purified by conventional means known to those skilled in the art, such as crystallization or column chromatography, to provide the α-halohydrin of general formula (11) or general formula (12).

Then, the α-halohydrin of general formula (11) or general formula (12) is treated with a base to provide the epoxide of general formula (13) or general formula (14). The preferred base for use in this step includes sodium hydroxide, potassium hydroxide, sodium methoxide, sodium ethoxide, potassium t-butoxide, and sodium hydride, among others. The amount of the base relative to the α-halohydrin is 1 to 10 molar equivalents, preferably 1 to 4 molar equivalents. As the reaction solvent, lower alcohols such as methanol, ethanol, etc., water, toluene, acetone, tetrahydrofuran, etc. can be used singly or in combination. This reaction is carried out by treating the α-halohydrin with said base at −10° C. to 80° C., preferably 0° C. to 40° C., for 10 to 180 minutes, preferably 30 to 60 minutes.

After the above reaction time, the reaction is stopped by adding diluted hydrochloric acid, an aqueous solution of ammonium chloride or the like and the reaction mixture is extracted with a solvent such as ethyl acetate, diethyl ether, toluene or the like. The extract is washed with saturated aqueous NaHCO$_3$ solution, saturated aqueous NaCl solution, etc. and dried over a desiccant such as anhydrous sodium sulfate, anhydrous magnesium sulfate, or the like. After the desiccant is filtered off, the filtrate is concentrated to provide the epoxide.

EXAMPLES

The following examples are intended to describe the present invention in further detail and should by no means be construed as defining the scope of the invention.

Example 1

Production of Phenacyl Chloride (I)

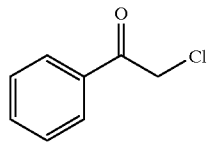

(I)

Under the atmosphere of nitrogen gas, diisopropylamine (2.42 g, 24.0 mmol) was dissolved in tetrahydrofuran (20 mL) and the solution was cooled to 0° C. To this solution was added n-butyllithium (1.6 M/hexane, 13.8 mL, 22.0 mmol) and the mixture was stirred for 10 minutes. After this solution was cooled to −30° C., monochloroacetic acid (0.946 g, 10.0 mmol) was added and the mixture was stirred for 30 minutes. To this solution was added ethyl benzoate (0.514 g, 3.33 mmol) and the mixture was stirred at −30° C. for 30 minutes. Thereafter, the temperature of the mixture was increased to 25° C. for 30 minutes. This reaction mixture was poured in 1N-HCl (50 mL) and extracted with ethyl acetate (50 mL×2). The extract was washed with saturated aqueous NaHCO$_3$ solution (50 mL×1) and water (50 mL×1) in that order and dried over anhydrous magnesium sulfate. After filtration, the filtrate was concentrated to provide a light-yellow oil (0.654 g). Comparative HPLC analysis of this product with an authentic sample revealed that the product is predominantly composed of phenacyl chloride (reaction yield 57.7%). Diisopropyl benzamide (reaction yield 3.4%) was also produced as a byproduct and 0.5% of the ethyl benzoate remained to be unreacted.

Examples 2 to 7

Production of Phenacyl Chloride (I)

Examples 2 to 7 were carried out in substantially the same manner as Example 1 using the following reaction temperature and time.

TABLE 1

| Example | Monochloro- acetic acid (mol. eq.) | Reaction temperature and time A | Reaction temperature and time B | Yield a | b | c |
|---|---|---|---|---|---|---|
| 2 | 3.0 | −30° C., 30 min. | −30° C.~rt, 30 min. | 64.0 | 11.8 | 0 |
| 3 | 3.0 | −78° C., 30 min. | −78° C.~rt, 1 hr. | 51.3 | 0 | 0.7 |
| 4 | 2.0 | −30° C., 30 min. | −30° C., 30 in. | 49.7 | 16.2 | 2.6 |
| 5 | 1.0 | −20° C., 1 hr. | −20° C.~rt, 1 hr. | 11.8 | 71.9 | 0.3 |
| 6 | 1.0 | 0° C.~rt, 3 hrs. | rt, 1 hr. | 28.7 | 49.4 | 2.3 |
| 7 | 1.0 | 0° C., 30 min. | 0° C.~rt, 1 hr. | 4.7 | 0.7 | 60.3 |

Example 8

Production of Phenacyl chloride (I)

Under the atomosphere of nitrogen gas, diisopropylamine (0.6605 g) was added to 6.67 mL of 0.9 M n-butylmagnesium chloride/tetrahydrofuran (6 mmol). The mixture was stirred a room temperature for 4 hours, after which it was cooled to 0° C. Then, a solution of 284 mg (3.0 mmol) of monochloroacetic acid and 136 mg (1 mmol) of methyl benzoate in 5 mL of tetrahydrofuran was added portionwise for 1 minutes. This mixture was stirred at 0° C. for 30 minutes and, while the temperature was allowed to rise to room temperature, further stirred for 30 minutes. This reaction mixture was poured in 1N-HCl (30 mL) and extracted with ethyl acetate (30 mL×2). The extract was washed with saturated aqueous NaHCO₃ solution (30 mL×1) and water (30 mL×1) in that order and dried over anhydrous magnesium sulfate. After filtration, the filtrate was concentrated to provide a light-yellow oil. Comparative HPLC analysis of this oil with an authentic sample revealed that the oil was predominantly composed of the objective phenacyl chloride (reaction yield 73.7%). Diisopropylbenzamide (reaction yield 0.4%) was obtained as a byproduct.

Example 9

Production of Phenacyl Chloride (I)

To 5 mL of tetrahydrofuran was added hexamethyldisilazane (6.6 mmol) under the atomosphere of nitrogen gas and after the solution was cooled to 0° C., 6.67 mL of 0.9 M n-butylmagnesium chloride/tetrahydrofuran (6 mmol) was added. The mixture was stirred at 0° C. for 10 minutes. Then, after cooling to −30° C., a solution of 284 mg (3.0 mmol) of monochloroacetic acid and 136 mg (1 mmol) of methyl benzoate in 5 mL of tetrahydrofuran was added dropwise for 5 minutes. This mixture was stirred at −30° C. for 30 minutes and, while the temperature was allowed to rise to room temperature, was further stirred for 1 hour. This reaction mixture was poured in 1N-HCl (50 mL) and extracted with ethyl acetate (50 mL×2). The extract was washed with saturated aqueous NaHCO₃ solution (50 mL×1) and water (30 mL×1) in that order and dries over anhydrous magnesium sulfate. After filtration, the filtrate was concentrated to provide a light-yellow oil. Comparative HPLC analysis of this oil with an authentic sample revealed that the oil was predominantly composed of the objective phenacyl chloride (reaction yield 84.3%). Methylbenzoate (reaction yield 17.5%) was obtained as a byproduct.

Example 10

Production of L-[N-(methoxycarbonyl) phenylalanyl]methyl chloride (II)

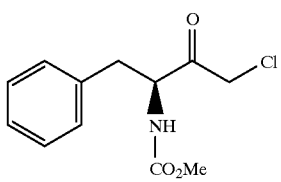

(II)

Figure 2:
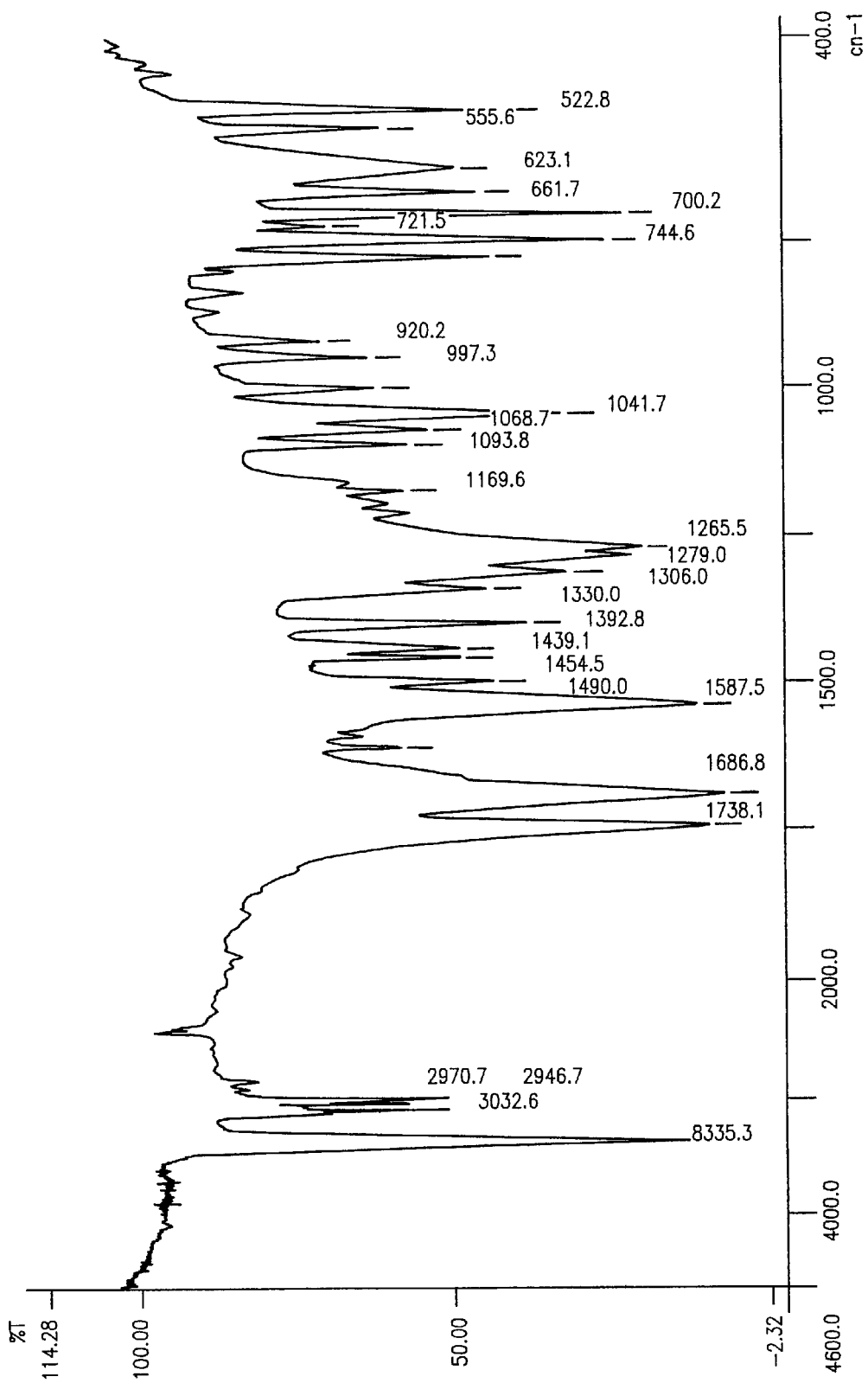
FIG. 2 shows an IR chart of L-[N-(methoxycarbonyl) phenylalanyl]methyl chloride (II) as obtained in Example 10.

Under the atmosphere of nitrogen gas, diisopropylamine (2.42 g, 24.0 mmol) was dissolved in tetrahydrofuran (20 mL) and the solution was cooled to 0° C. Then, n-butyllithium (1.6 M/hexane, 13.8 mL, 22.0 mmol) was added and the mixture was stirred for 10 minutes. After the mixture was cooled to −30° C., monochloroacetic acid (0.946 g, 10.0 mmol) was added and the mixture was further stirred for 30 minutes. In a separate reaction vessel, L-N-(methoxycarbonyl)phenylalanine methyl ester (purity 83.0%, 0.950 g, 3.33 mmol) was dissolved in tetrahydrofuran (10 mL) under the atomosphere of nitrogen gas and, after addition of n-butyllithium (1.6 M/hexane, 2.1 mL, 3.33 mmol) at −78° C., the mixture was further stirred for 10 minutes. To this mixture was added trimethylsilyl chloride (0.363 g, 3.33 mmol) and the temperature of the mixture was allowed to rise to room temperature for 30 minutes. This solution was added gradually to the above lithium diisopropylamide solution cooled at −30° C. beforehand and the reaction was conducted at −30° C. for 30 minutes. Then, while the temperature of the reaction mixture was allowed to rise to room temperature, the react-on was further carried out for 30 minutes. This reaction mixture was poured in 1N-HCl (50 mL) and extracted with ether acetate (50 mL×2). The extract was washed with saturated aqueous NaHCO₃ solution (50 mL×1 and water (30 mL×1) in that order and dried over anhydrous magnesium sulfate. After filtration, the filtrate was concentrated to provide light-yellow crystals (0.888 g). This crystal crop was recrystallized from ethyl acetate/hexane (2 mL/10 mL) to provide white crystals of L-[N-(methoxycarbonyl)phenylalanyl]methyl chloride (0.261 g, yield after recrystallization: 30.7%). The reaction yield of the objective compound as calculated from the result of HPLC analysis of the above extract was 41.6%. The residue of the starting compound N-methoxycarbonylphenylalanine methyl ester was found to be 12.3%. The NMR and IR spectra of the product L-[N-(methoxycarbonyl)phenylalanyl]methyl chloride are presented in FIGS. 1 and 2.

Example 11

Production of L-[N-(methoxycarbonyl) phenylalanyl]methyl chloride (II)

Under the atomosphere of nitrogen gas, diisopropylamine (4.90 g, 48.4 mmol) was dissolved in tetrahydrofuran (50 mL) and the solution was cooled to 0° C. To this solution was added n-butyllithium (1.66 M/hexane, 26.5 mL, 44 mmol) and the mixture was stirred for 10 minutes. After cooling to −30° C. a solution of monochloroacetic acid (1.89 g, 20.0 mmol) in tetrahydrofuran (10 mL) was added and the mixture was stirred for 30 minutes. To this solution was gradually added a solution of L-N-(methoxycarbonyl) phenylalanine methyl ester (purity 88.0%, 1.348 g, 5 mmol) in tetrahydrofuran (10 mL) and the reaction was carried out at −30° C. for 30 minutes. Then, while the temperature of the reaction mixture was allowed to rise to room temperature, the reaction was further carried out for 30 minutes. This reaction mixture was poured in 1N-HCl (50 ml) and extracted with ethyl acetate (50 mL×2). The extract was washed with saturated aqueous $NaHCO_3$ solution (50 mL×1) and water (50 mL×1) in that order and dried over anhydrous magnesium sulfite. After filtration, the filtrate was concentrated to provide light-yellow crystals (1.68 g). This crystal crop was recrystallized from ethyl acetate/hexane (2 mL/10 mL) to provide white crystals of L-[N-(methoxycarbonyl)phenylalanyl]methyl chloride (0.546 g, yield after recrystallization 42.7%).

Example 12

Production of L-[N-(methoxycarbony)phenylalanyl] methyl chloride (II)

Under the atmosphere of nitrogen gas, diisopropylamine (0.668 g) was added to 6.67 mL of 0.9 M n-butylmagnesium chloride/tetrahydrofuran (6 mmol) and the mixture was stirred at 0° C. for 10 minutes. Then, a solution of 284 mg (3.0 mmol) of monochloroacetic acid and 201 mg (0.73 mmol) of L-N-(methoxycarbonyl)phenylalanine methyl ester (purity 88.0%) in 5 mL of tetrahydrofuran was added for 3 minutes and while the temperature was allowed to rise to room temperature, the mixture was stirred for 1 hour. This reaction mixture was poured in 1N-HCl (30 mL) and extracted with ethyl acetate (30 mL×2). The extract was washed with saturated aqueous $NaHCO_3$ solution (50 mL×1) and saturated aqueous NaCl solution (50 mL×1) in that order and dried over anhydrous magnesium sulfate. After filtration, the filtrate was concentrated to provide light-yellow crystals (0.253 g). This crystal crop was recrystallized from ethyl acetate/hexane (0.5 mL/5 mL) to provide white crystals of L-[N-(methoxycarbonyl)phenylalanyl] methyl chloride (0.042 g, yield after recrystallization: 21.9%).

Example 13

Production of L-[N-(benzyloxycarbonyl) phenylalanyl]methyl chloride (III)

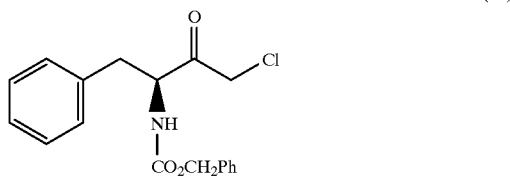

(III)

Figure 3:
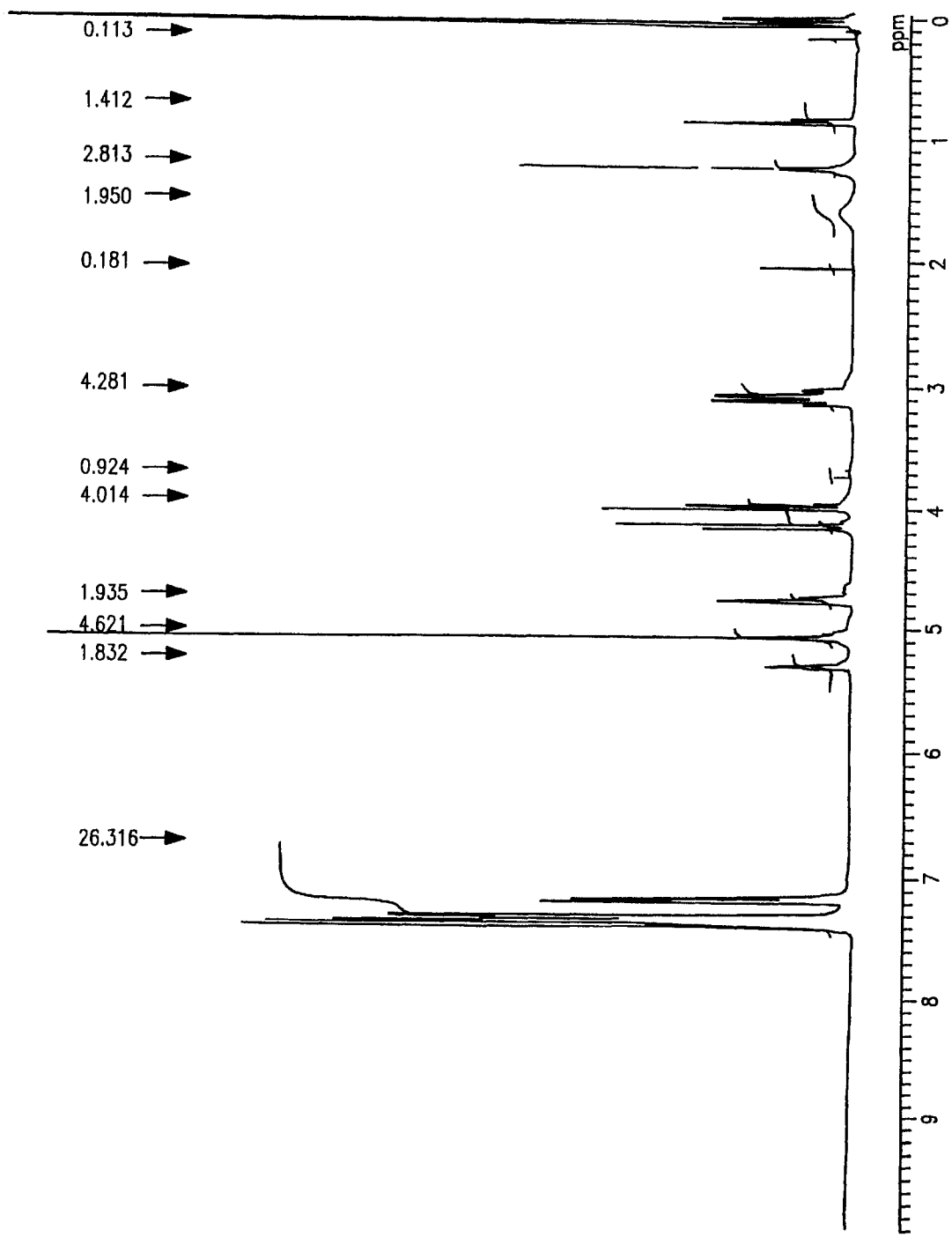
FIG. 3 shows an NMR chart of L-[N-(benzyloxycarbonyl) phenylalanyl]methyl chloride (III) as obtained in Example 13.
Figure 4:
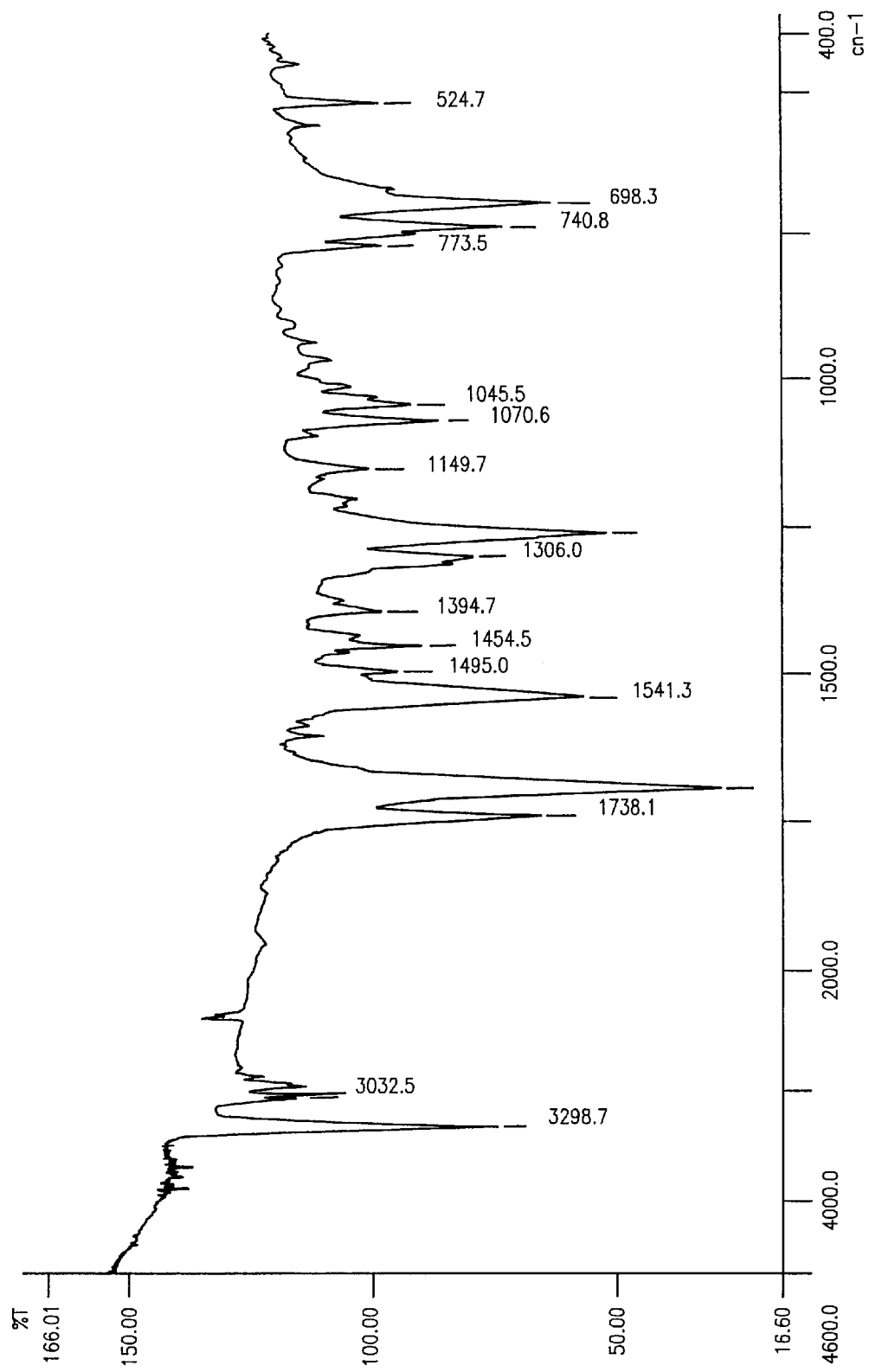
FIG. 4 shows an IR chart of L-[N-(benzyloxycarbonyl) phenylalanyl]methyl chloride (III) as obtained in Example 13.

Using L-N-(benzyloxycarbonyl)phenylalanine methyl ester (purity 89.8%, 1.16 g, 3.33 mmol) in lieu of L-N-(methoxycarbonyl)phenylalanine methyl ester, the reaction procedure of Example 10 was otherwise repeated to provide light-yellow crystals (0.99 g). This crystal crop was recrystallized from ethyl acetate-hexane (2 mL–10 mL) to provide white crystals of L-[N-(benzyloxycarbonyl)phenylalanyl] methyl chloride (0.340 g, yield after recrystallization: 32.3%). The NMR and IR spectra of this L-[N-(benzyloxycarbonyl)phenylalanyl]methyl chloride are presented in FIGS. 3 and 4, respectively.

Example 14

Production of L-[N-(t-butoxycarbonyl)phenylalanyl] methyl chloride (IV)

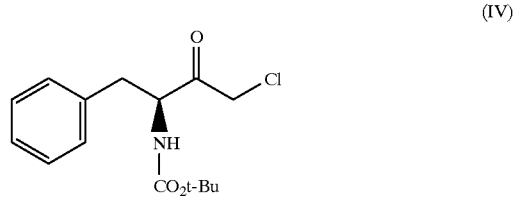

(IV)

Figure 5:
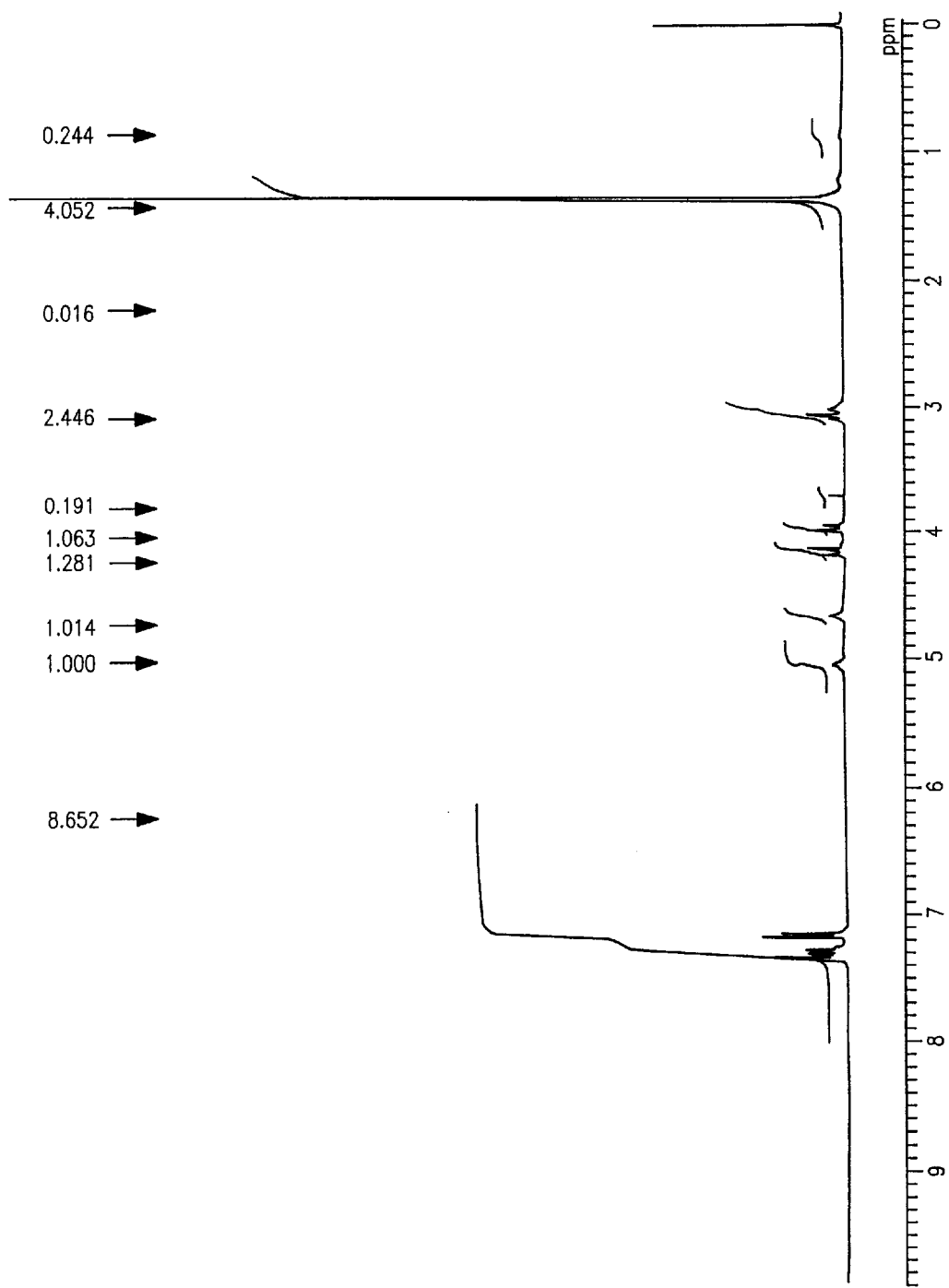
FIG. 5 shows an NMR chart of L-[N-(t-butoxycarbonyl) phenylalanyl]methyl chloride (IV) as obtained in Example 14.
Figure 6:
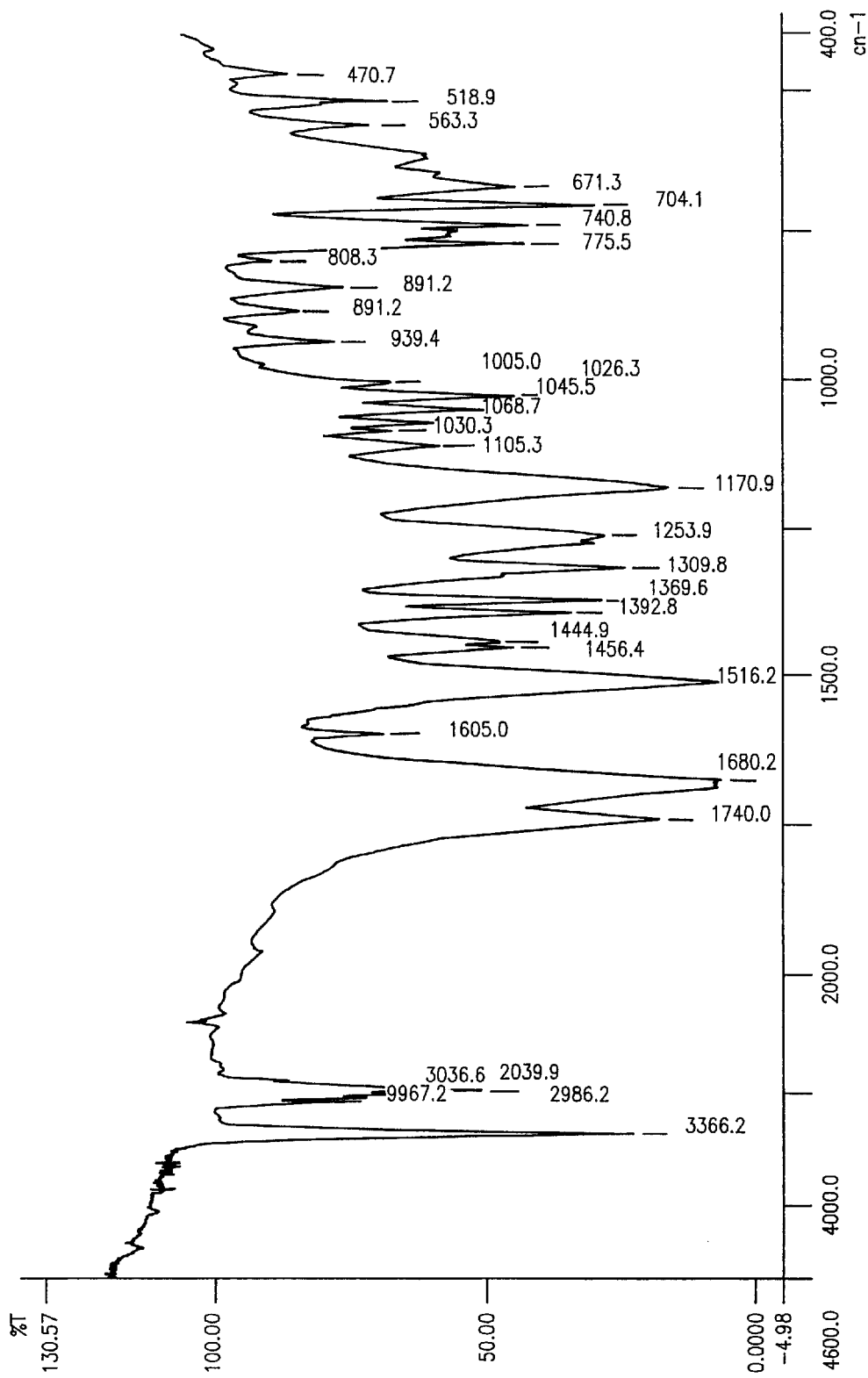
FIG. 6 shows an IR chart of L-[N-(t-butoxycarbonyl) phenylalanyl]methyl chloride (IV) as obtained in Example 14.

Under the atmosphere of nitrogen gas, diisopropylamine (3.68 g, 37 mmol) was dissolved in tetrahydrofuran (40 ml) and the solution was cooled to 0° C. To this solution was added n-butyllithium (1.6 M/hexane, 30 mL, 48 mmol) and the mixture was stirred for 10 minutes. After this solution was cooled to −30° C., monochloroacetic acid (2.25 g, 23.8 mmol) was added and the mixture was stirred for 30 minutes. In a separate reaction vessel, L-N-(t-butoxycarbonyl)phenylalanine methyl ester (purity 87.0%, 1.61 g, 3 mmol) was dissolved in tetrahydrofuran (10 mL) under the atmosphere of nitrogen gas and, after addition of n-butyllithium (1.6 M/hexane, 3.17 mL, 5 mmol) at −78° C., the mixture was further stirred for 10 minutes. To this mixture was added trimethylsilyl chloride (0.545 g, 5 mmol) and the temperature of the mixture was allowed to rise to room temperature for 30 minutes. This solution was added gradually to the above lithium diisopropylamide solution cooled at −0° C. beforehand and the reaction was conducted at −30° C. for 30 minutes. Then, while the temperature of the reaction mixture was allowed to rise to room temperature, the reaction was further carried out for 60 minutes. This reaction mixture was poured in saturated aqueous $NH_4Cl$ solution (50 mL) and extracted with ethyl acetate (50 mL×2). The extract was washed with saturated aqueous $NaHCO_3$ solution (50 mL×1) and water (50 mL×1) in that order and dried over anhydrous magnesium sulfate. After filtration, the filtrate was concentrated to provide light-yellow crystals (2.062 g). This crystal crop was recrystallized from ethyl acetate/hexane (2 mL/10 mL) to provide white crystals of L-[N-(t-butoxycarbonyl)phenylalanyl] methyl chloride (0.37 g, yield 25%). The NMR and IR spectra of the product L-[N-(t-butoxycarbonyl) phenylalanyl]methyl chloride are presented in FIGS. 5 and 6, respectively.

$[\alpha]_D^{25}$=−34.92 (c=1.0, EtOH)

m.p.: 103.5 to 105.2° C.

Example 15

Production of L-[N-(methoxycarbonyl) phenylalanyl]methyl chloride (II)

Under the atmosphere of nitrogen gas, a solution of L-N-(methoxycarbonyl)phenylalanine methyl ester (purity 94%, 25.33 g, 100 mmol), sodium monochloroacetate (17.48 g, 150 mmol) and magnesium chloride (14.29 g, 130 mmol) in tetrahydrofuran (78.3 ml) was stirred at 20 through 25° C. for 3 hours (solution A). Separately, also under the atmosphere of nitrogen gas, diisopropylamine (44.32 g, 440 mmol) was added to a solution of n-butylmagnesium chloride (2.5 mol/kg solution, 159.7 g, 400 mmol) in tetrahydrofuran (12.8 ml) for 30 minutes at 40° C. and the mixture was further stirred at 40° C. for 2 hours (solution B). At an internal temperature of about 10° C., this solution B was added to the above solution A for about 30 minutes. After completion of this addition, the internal temperature was increased to 40° C. and the mixture was further stirred for 2 hours. To this reaction mixture was added a solution of 35% HCl (91.7 g) and water (200 ml) and the mixture was stirred for 30 minutes for hydrolysis. The organic phase was separated and washed with saturated aqueous NaHCO$_2$ solution (200 ml) and saturated aqueous NaCl solution (20 ml) in that order. The organic phase was then concentrated under reduced pressure to give a light-yellow solid (23.5 g). Quantitative analysis by HPLC showed the formation of 22.45 g (87.8 mmol) of L-[N-(methoxycarbonyl)phenylalanyl]methyl chloride (II). This solid was recrystallized from isopropyl alcohol to provide white crystals of L-[N-(methoxycarbonyl)phenylalanyl]methyl chloride (19.8 g, 77.6 mmol, yield 77.6%).

Example 16

Production of L-[N-(methoxycarbonyl) phenylalanyl]methyl chloride (II)

Under the atmosphere of nitrogen gas, t-butyl magnesium chloride (2M/L THF, 30.0 ml, 60 mmol) was added to a solution of L-N-(methoxycarbonyl)phenylalanine methyl ester (2.37 g, 10 mmol), sodium monochloroacetate (1.74 g, 15 mmol) and triethylamine (1.52 g, 15 mmol) in tetrahydrofuran (40 ml) for about 3 hours at an internal temperature not exceeding 10° C. After completion of this addition, the internal temperature was increased to 20° C. and the mixture was further stirred for 2 hours. Then, a solution of 35% HCl (10.0 g) and water (100 ml) and toluene (100 ml) were added and the mixture was stirred for 30 minutes for hydrolysis. The organic phase was separated and washed with saturated aqueous NaHCO$_3$ solution (50 ml) and saturated aqueous NaCl solution (50 ml) in that order. Quantitative analysis of the organic phase by HPLC revealed the formation of 2.17 g (8.51 mmol, yield 85%) of L-[N-(methoxycarbonyl)phenylalanyl]methyl chloride (II).

Example 17

Production of L-[N-(methoxycarbonyl) phenylalanyl]methyl chloride (II)

Under the atmosphere of nitrogen gas, a solution of monochloroacetic acid (9.45 g, 0.1 mol) in tetrahydrofuran (42 ml) was added dropwise to a solution of metallic magnesium (1.216 g, 50 mmol) and magnesium chloride (4.76 g, 50 mmol) in tetrahydrofuran (20 ml) at an internal temperature of about 30° C. and the mixture was further stirred at room temperature for 24 hours. To this solution was added L-N-(methoxycarbonyl)phenylalanine methyl ester (15.82 g, 66.6 mmol (solution A). Separately, under the atmosphere of nitrogen gas, diisopropylamine (29.65 g, 290.4 mmol) was added to a solution of n-butylmagnesium chloride (2.5 mol/kg, 106.36 g, 266.4 mmol) in tetrahydrofuran (8.5 ml) for 30 minutes at 40° C. and the mixture was further stirred at 40° C. for 2 hours (solution B). At an internal temperature of about 10° C., this solution B was added to the above solution A for about 30 minutes. After completion of this addition, the internal temperature was increased to 40° C. and the mixture was further stirred for 2 hours. To this reaction mixture was added a solution of 35% HCl (66.7 g) and water (260 ml) and the mixture was stirred for 30 minutes for hydrolysis. The organic phase was separated and washed with saturated aqueous NaHCO$_3$ solution (260 ml, and saturated aqueous NaCl solution (260 ml) in that order. The organic phase was then concentrated under reduced pressure to give a light-yellow solid (16.5 g). Quantitative analysis by HPLC showed the formation of 14.4 g (56.6 mmol, yield 85%) of L-[N-(methoxycarbonyl) phenyl alanyl]methyl chloride (II).

Example 18

Production of L-[N-(methoxycarbonyl) phenylalanyl]methyl chloride (II)

Under the atmosphere of nitrogen gas, diisopropylamine (668 mg, 6.60 mmol) was added to n-butylmagnesium chloride (6.67 ml, 6 mmol) around room temperaure and the mixture was refluxed for 30 minutes (solution A). Separately, a solution of sodium monochloroacetate (669 mg, 5.74 mmol) and zinc chloride (408.8 mg, 3 mmol) in tetrahydrofuran (5 ml) was stirred around room temperature for 15 hours (solution B). In the neighborhood of room temperature, this solution B was added to the above solution A followed by addition of a solution of L-N-(methoxycarbonyl)phenylalanine methyl ester (404 mg, 1.71 mmol) in tetrahydrofuran (5 ml) at 0 to 5° C. After completion of this addition, the mixture was stirred at 0° C. through room temperature for 1 hour and then refluxed for 30 minutes. To this reaction mixture was added 1N-HCl (30 ml) and the mixture was stirred for 30 minutes for hydrolysis. The organic phase was then separated. Quantitative analysis of the organic phase by HPLC revealed the formation of 263.1 mg 1.3 mmol) of L-[N-(methoxycarbonyl) phenylalanyl]methyl chloride (II).

Example 19

Production of L-[N-(methoxycarbonyl) phenylalanyl]methyl chloride (II)

Under the atmosphere of nitrogen gas, t-butylmagnesium chloride (2M/L THF, 30.0 ml, 60 mmol) was added to a solution of L-N-(methoxycarbonyl) phenylalanine methyl ester (2.37 g, 10 mmol), sodium monochloroacetate (1.74 g, 15 mmol) and 2,6-lutidine (3.21 g, 30 mmol) in tetrahydrofuran (40 ml) for about 3 hours at an internal temperature not exceeding 10° C. After completion of this addition, the internal temperature was increased to 20° C. and the mixture was further stirred for 2 hours. Then, a solution of 35% HCl (10.0 g) and water (100 ml) and toluene (100 ml) were added and the mixture was stirred for 30 minutes for hydrolysis. The organic phase was separated and washed with saturated aqueous NaHCO$_3$ solution (50 ml) and saturated aqueous NaCl solution (50 ml) in that order. Quantitative analysis of the organic phase by HPLC revealed the formation of 2.17 g (8.51 mmol, yield 85%) of L-[N-(methoxycarbonyl)phenylalanyl]methyl chloride (II).

Example 20

Production of L-[N-(methoxycarbonyl) phenylalanyl]methyl chloride (II)

Under the atmosphere of nitrogen gas, t-butylmagnesium chloride (2M/L THF, 20.0 ml, 40 mmol)

was added to a solution of L-N-(methoxycarbonyl) phenylalanine nethyl ester (2.37 g, 10 mmol), sodium monochloroacetate (1.74 g, 153 mmol) and 2,6-lutidine (3.21 g, 30 mmol) in tetrahydrofuran (4 ml) for about 3 hours at an internal temperature not exceeding 10° C. After completion of this addition, the internal temperature was increased to 20° C. and the mixture was further stirred for 2 hours. Then, a solution of 35% HCl (10.0 g) and water (100 ml) and toluene (100 ml) were added and the mixture was stirred for 30 minutes for hydrolysis. The organic phase was separated and washed with saturated aqueous $NaHCO_3$ solution (50 ml) and saturated aqueous NaCl solution (50 ml) in that order. Quantitative analysis of the organic phase by HPLC revealed the formation of 1.87 g (7.31 mmol, yield 73%) of L-[N-(methoxycarbonyl)phenylalanyl]methyl chloride (II).

Example 21

Production of L-[N-(methoxycarbonyl) phenylalanyl]methyl chloride (II)

Under the atomosphere of nitrogen gas, t-butylmagnesium chloride (2M/L THF, 20.0 ml, 40 mmol was added to a solution of L-N-(methoxycarbonyl) phenylalanine methyl ester (474 mg, 2 mmol) in tetrahydrofuran (1 ml) dropwise for about 15 minutes at an internal temperature of about 20° C. with stirring. To this solution was added a solution of monochloroacetic acid (284 mg, 3 mmol) and triethylamine (610 mg, 12 mmol) in tetrahydrofuran (2 ml) dropwise for about 15 minutes at an internal temperature of about 20° C. with stirring. After completion of this dropwise addition, the mixture was further stirred for 2 hours. Then, a solution of 35% HCl (2.5 g) and water (20 ml) was added, and the mixture was stirred for 15 minutes for hydrolysis and extracted with toluene (25 ml). The organic phase was washed with saturated aqueous $NaHCO_3$ solution (10 ml) and saturated aqueous NaCl solution (10 ml) in that order. Quantitative analysis of the organic phase by HPLC revealed the formation of 435 mg (1.70 mmol, yield 85%) of L-[N-(methoxycarbonyl)phenylalanyl]methyl chloride (II).

Example 22

Production of L-[N-(ethoxycarbonyl)phenylalanyl] chloride (V)

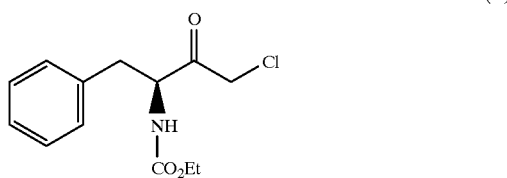

(V)

Under the atomosphere of nitrogen gas, a solution of L-N-(ethoxycarbonyl)phenylalanine methyl ester (5.02 g, 20 mmol), sodium monochloroacetate (3.49 g, 30 mmol) and magnesium chloride (2.86 g, 30 mmol) in tetrahydrofuran (18.3 ml) was stirred at 20 to 25° C. for 3 hours (solution A). Separately, under the atomosphere of nitrogen gas, diisopropylamine (9.92 g, 88 mmol) was added to a solution of n-butylmagnesium chloride (2.5 mol/kg, 31.6 g, 80 mmol) in tetrahydrofuran (10 ml) for 30 minutes at 40° C. and the mixture was further stirred at 40° C. for 2 hours (solution B).

Figure 7:
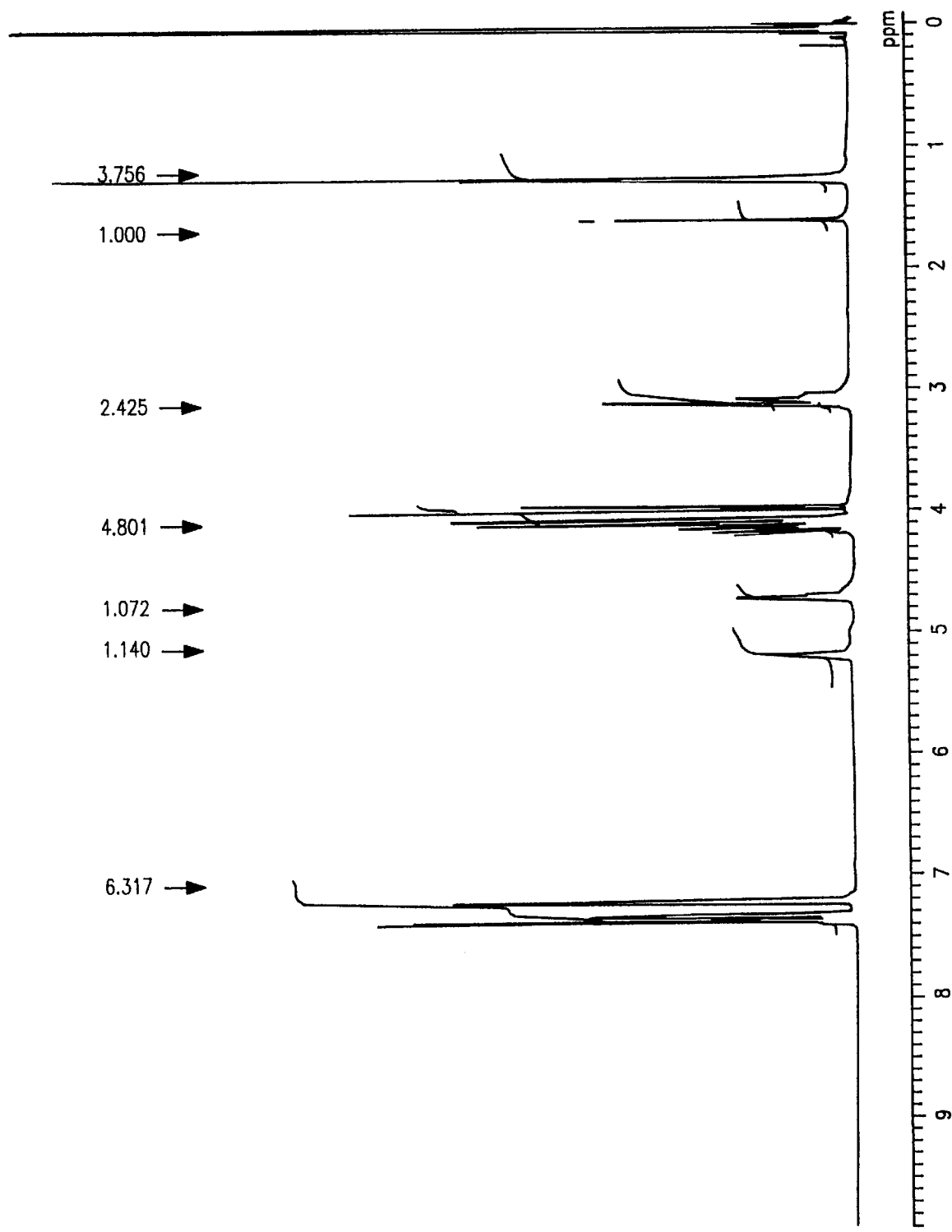
FIG. 7 shows an NMR chart of L-[N-(ethoxycarbonyl) phenylalanyl]methyl chloride (V) as obtained in Example 22.
Figure 8:
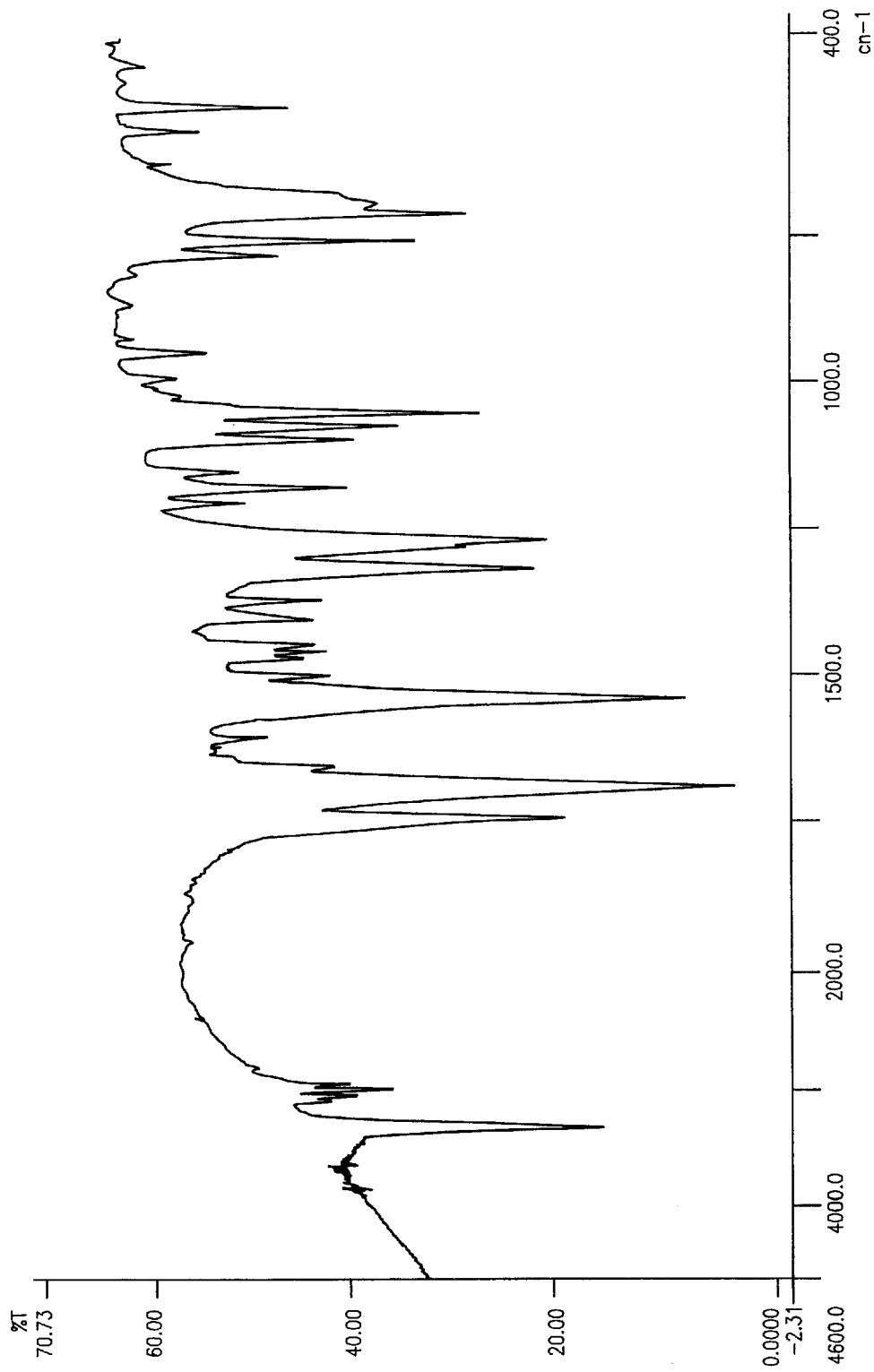
FIG. 8 shows an IR chart of L-[N-(ethoxycarbonyl) phenylalanyl]methyl chloride (V) as obtained in Example 22.

At an internal temperature of 10° C. to 15° C., this solution B was added to the above solution A for about 30 minutes. After completion of this addition, the internal temperature was increased to 40° C. and the mixture was further stirred for 1.5 hours. To this reaction mixture was added a solution consisting of 10% sulfuric acid (132 g) and ethyl acetate (80 ml) and the mixture was stirred for 30 minutes for hydrolysis. The organic phase was separated and washed with saturated aqueous $NaHCO_3$ solution (60 ml) and saturated aqueous NaCl solution (60 ml) in that order. The organic phase was then concentrated under reduced pressure to give a light-yellow solid (5.41 g). This solid was recrystallized from toluene/hexane to provide white crystals of L-[N-(ethoxycarbonyl)phenylalanyl]methyl chloride (V) (2.04 g, 7.95 mmol, yield 79.5%). The NMR and IR spectra of this product L-[N-(ethoxycarbonyl)phenylalanyl]methyl chloride (V) are presented in FIGS. 7 and 8, respectively.

$[\alpha]_D^{25} = -47.92$ (c=1.06, EtOH)

m.p. 83.0 to 84.0° C.

Example 23

Production of L-[N-(t-butoxycarbonylphenylalanyl] methyl chloride (IV)

Under the atomosphere of nitrogen gas, a solution of L-N-(t-butoxycarbonyl)phenylalanine methyl ester (20.64 g, 71.6 mmol), sodium monochloroacetate (12.5 g, 107.4 mmol) and magnesium chloride (10.23 g, 107.4 mmol) in tetrahydrofuran (59 ml) was stirred at 20 to 25° C. for 3 hours (solution A). Separately, under the atomosphere of nitrogen gas, diisopropylamine (31.9 g, 315 mmol) was added to a solution of n-butylmagnesium chloride (2.5 mol/kg, 115 g, 286.4 mmol) in tetrahydrofuran (9.2 ml) for 30 minutes at 40° C. and the mixture was further stirred at 40° C. for 2 hours (solution B). At an internal temperature of about 10° C., this solution B was added to the above solution A for about 30 minutes. After completion of this addition, the internal temperature was increased to 40° C. and the mixture was further stirred for 2 hours. To this reaction mixture was added a solution consisting of 60% sulfuric acid (45.0 g) and water (170 ml) and the mixture was stirred for 30 minutes for hydrolysis. The organic phase was separated and washed with 5% aqueous $NaHCO_3$ solution (90 ml) and 5% aqueous sodium sulfate solution (90 ml) in that order. The organic phase was then concentrated under reduced pressure to provide a light-yellow solid (20.5 g). Quantitative analysis by HPLC showed the formation of 18.36 g (61.5 mmol, yield 86%) of L-[N-(t-butoxycarbonyl) phenylalanyl]methyl chloride (IV). This solid was recrystallized from toluene-hexane to provide white crystals of L-[N-(t-butoxycarbonyl)phenylalanyl]methyl chloride (IV) (17.1 g, 57.3 mmol, yield 80%).

Example 24

Production of L-[N-(methoxycarbonyl) phenylalanyl]chlorohydrin (VI)

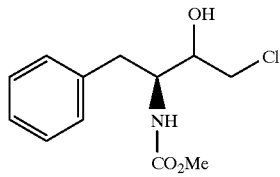

(VI)

Figure 9:
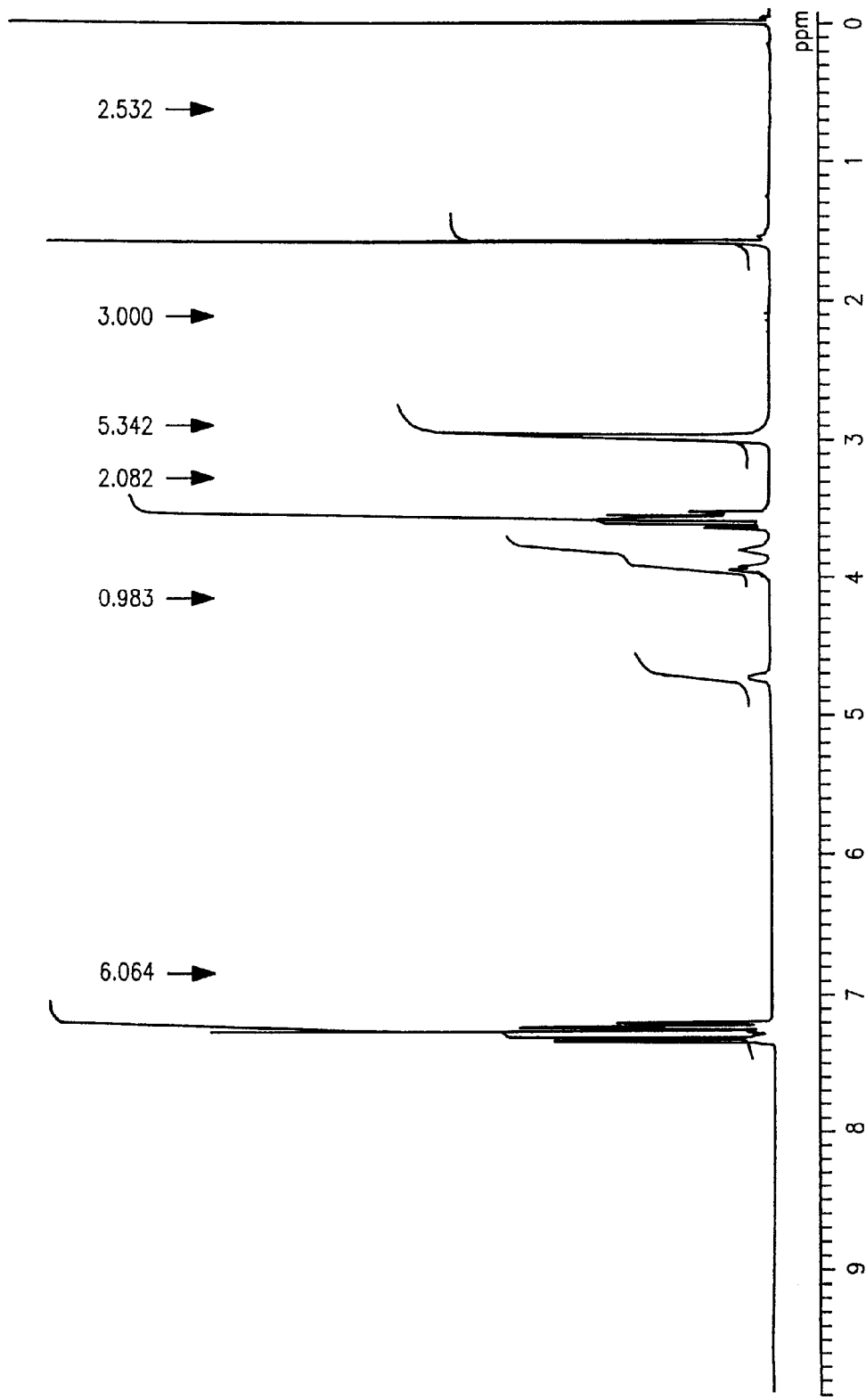
FIG. 9 shows an NMR chart of L-[N-(methoxycarbonyl) phenylalanyl]chlorohydrin (VI) as obtained in Example 24.
Figure 10:
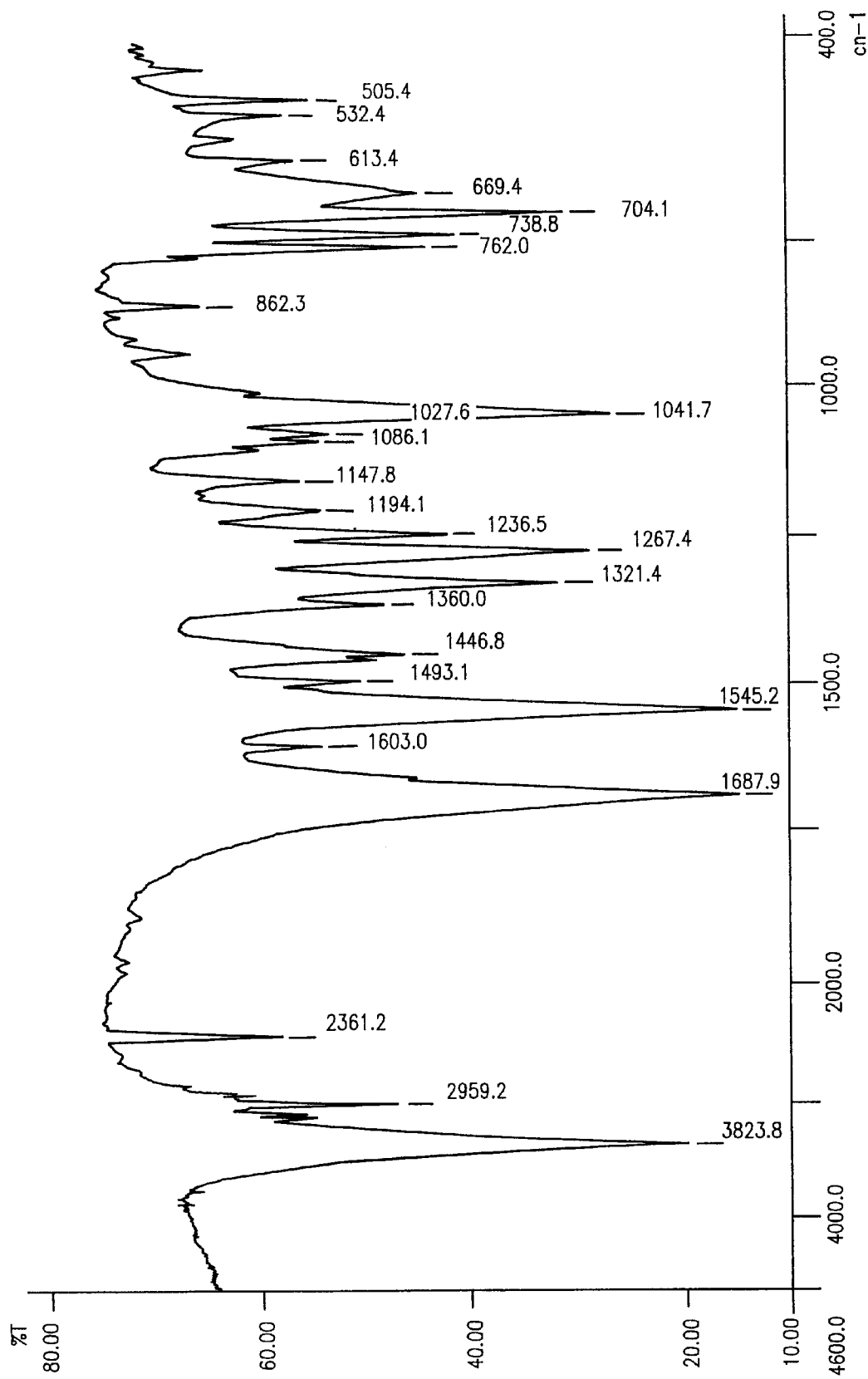
FIG. 10 shows an IR chart of L-[N-(methoxycarbonyl) phenylalanyl]chlorohydrin (VI) as obtained in Example 24.

To an ice-cold solution of L-[N-(methoxycarbonyl) phenylalanyl]methyl chloride (2.00 g, 7.82 mmol) in ethanol (20 mL) was added sodium borohydride (0.296 g, 7.82 mmol), and the mixture was stirred at that temperature for 30 minutes. This reaction mixture was poured in diluted sulfuric acid (0.383 g, 391 mmol dissolved in 50 mL of water) and extracted with ethyl acetate (100 mL×2). The extract was washed with saturated aqueous NaHCO$_3$ solution (50 mL×1) and water (50 mL×1) in that order and dried over anhydrous magnesium sulfate. After filtration, the filtrate was concentrated to provide white crystals. This crystal crop was recrystallized from ethanol/ethyl acetate hexane (1 mL/2 mL, 10 mL) to provide white crystals of L-[N-(methoxycarbonyl)phenylalanyl]chlorohydrin (VI) (1.39 g, erythro/threo=98.6:1.4). Based on the result of HPLC analysis of the above extract, the reaction yields were 74.4% for the erythro-form and 20.8% for the threo-form. The NMR and IR spectra of the product L-[N-(methoxycarbonyl) phenylalanyl]chlorohydrin (VI) are presented in FIGS. 9 and 10, respectively.

Example 25

Production of L-[N-(methoxycarbonyl) phenylalanyl]epoxide (VII)

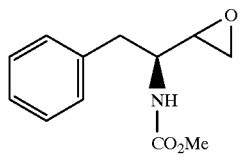

(VII)

Figure 11:
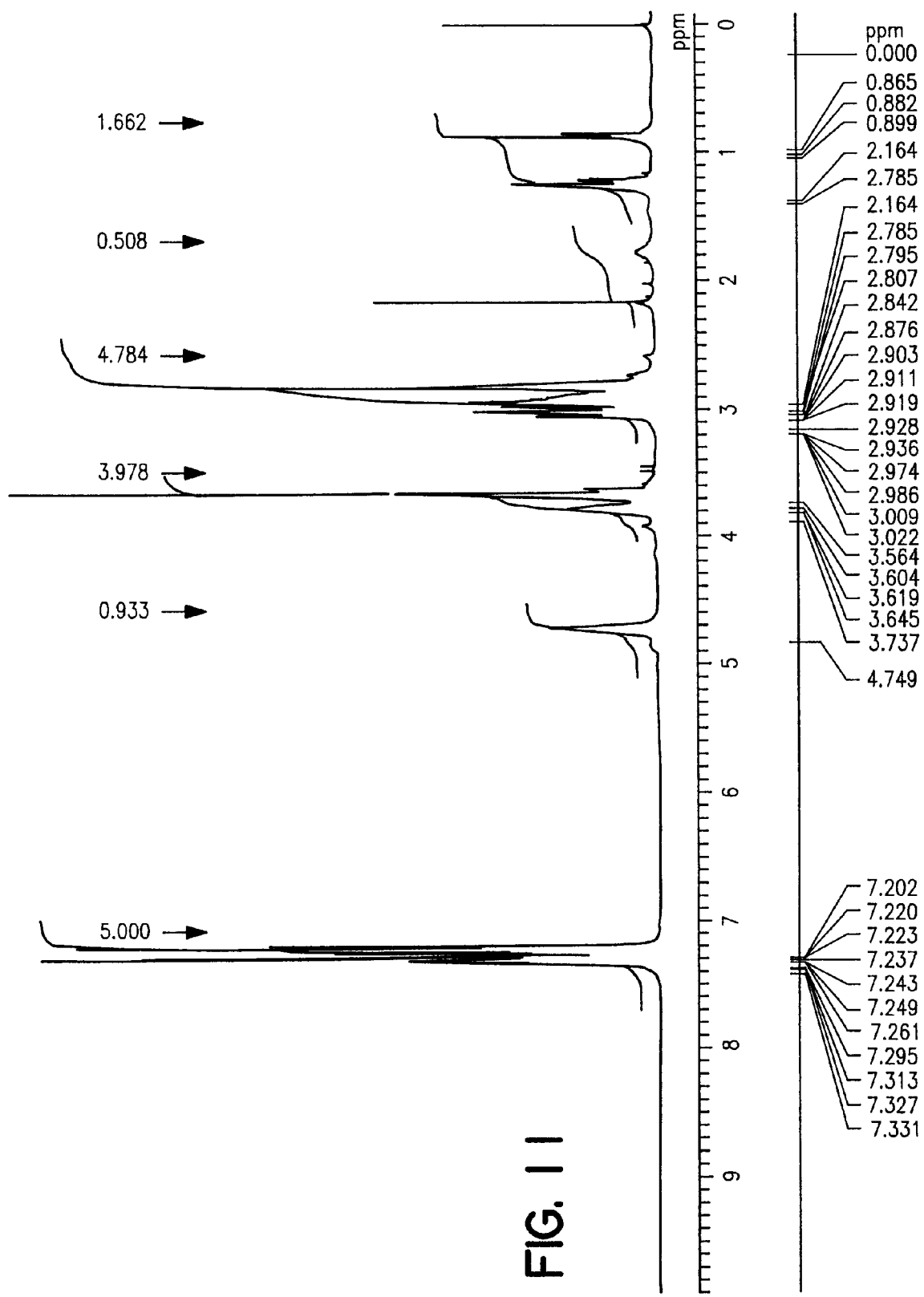
FIG. 11 shows an NMR chart of L-(N-methoxycarbonyl) phenylalanyl epoxide (VII) as obtained in Example 25.
Figure 12:
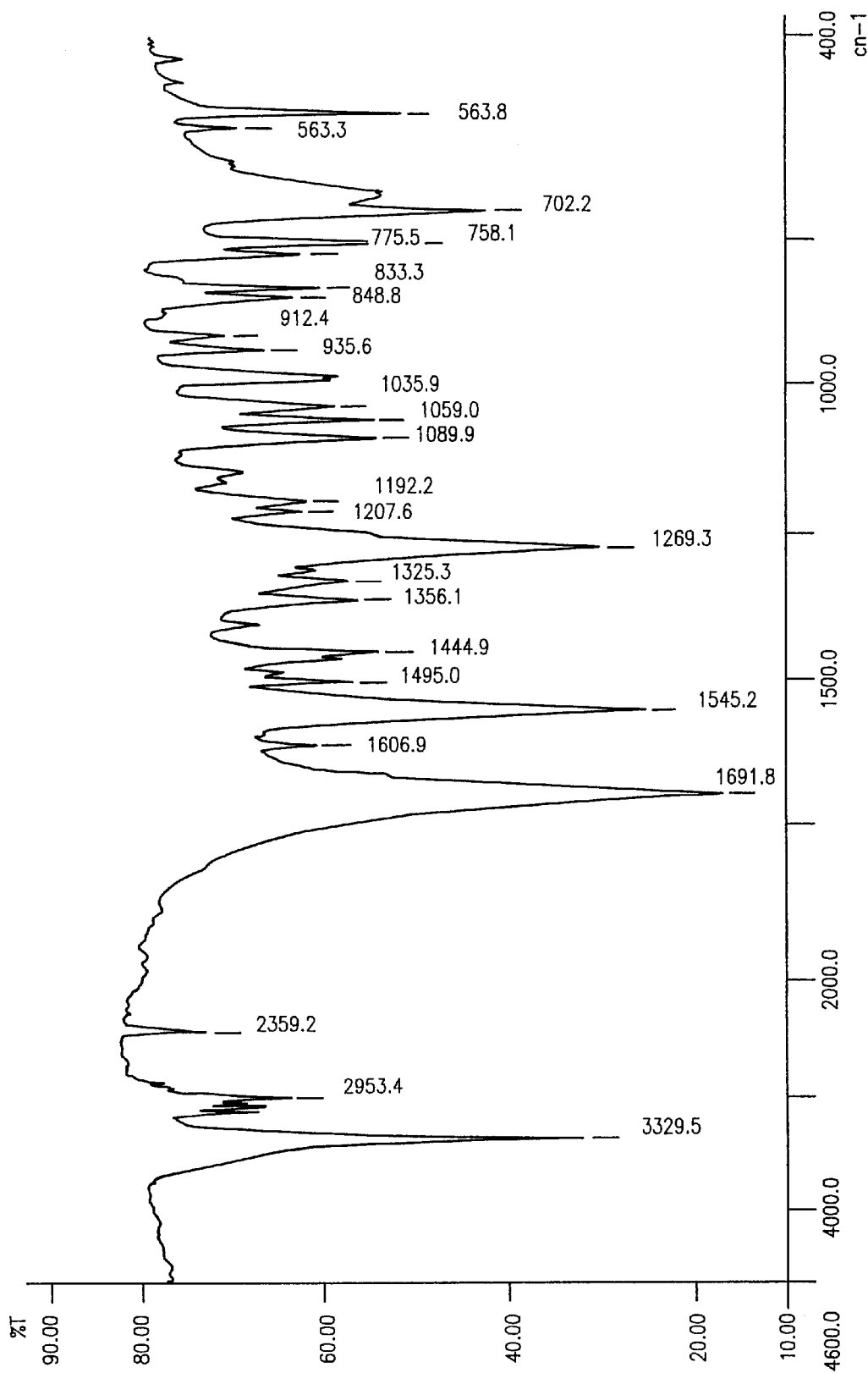
FIG. 12 shows an IR chart of L-(N-methoxycarbonyl) phenylalanyl epoxide (VII) as obtained in Example 25.

In methanol (5 mL) was dissolved L-[N-(methoxycarbonyl)phenylalanyl]chlorohydrin (VI) (0.077 g, 0.30 mmol) as obtained in Example 24. To this solution was added a solution of sodium methoxide (0.080 g, 1.50 mmol) in methanol (5 mL) at room temperature and the mixture was stirred at that temperature for 1 hour. This reaction mixture was poured in water (15 mL) and extracted with ethyl acetate (20 mL×2). The extract was washed with water (10 mL×1) and dried over anhydrous magnesium sulfate. After filtration, the filtrate was concentrated to provide L-[N-(methoxycarbonyl)phenylalanyl]epoxide as colorless oil (0.050 g). The NMR and IR spectra of the product L-[N-(methoxycarbonyl)phenylalanyl] epoxide (VII) are presented in FIGS. 11 and 12, respectively.

Example 26

Production of L-[N-(t-butoxycarbonyl)phenylalanyl] chlorohydrin (VII)

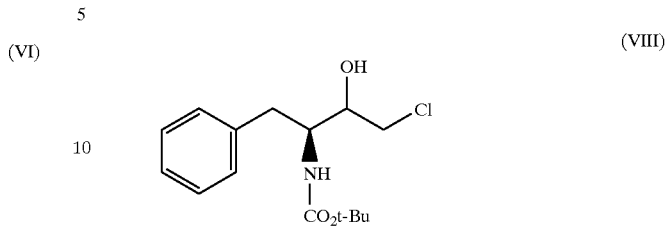

(VIII)

Figure 13:
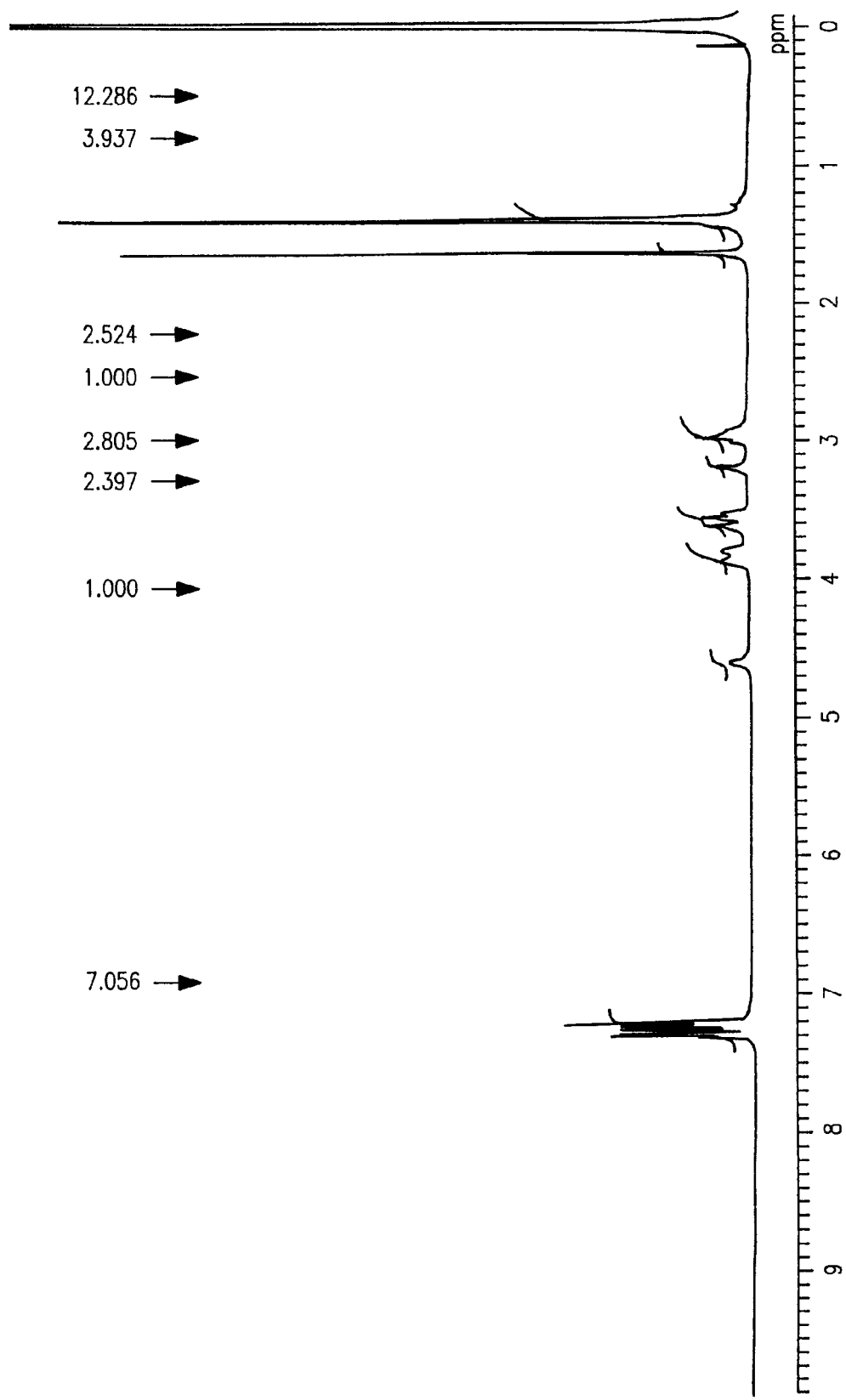
FIG. 13 shows an NMR chart of L-[N-(t-butoxycarbonyl) phenylalanyl]chlorohydrin (VIII) as obtained in Example 26.
Figure 14:
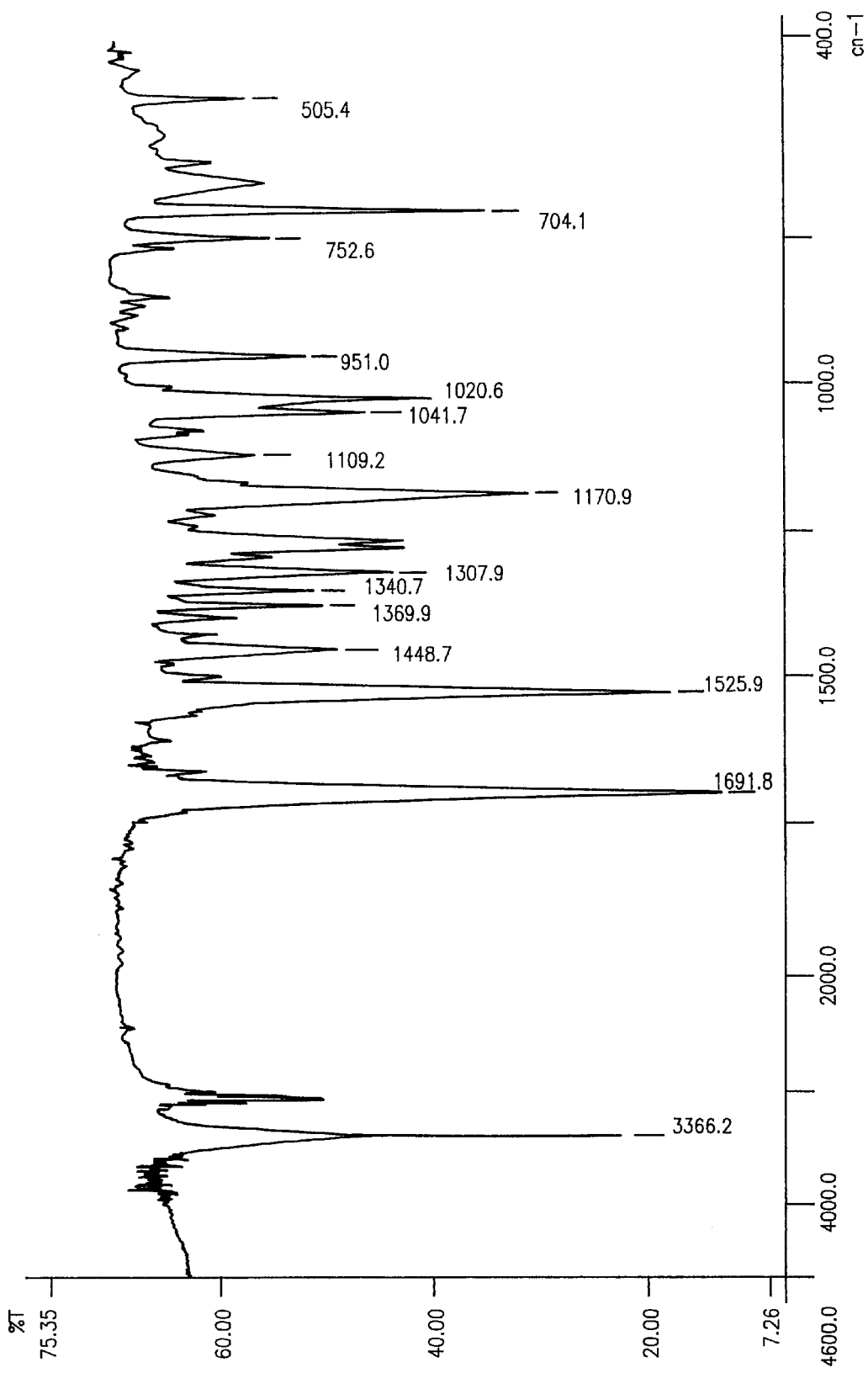
FIG. 14 shows an IR chart of L-[N-(t-butoxycarbonyl) phenylalanyl]chlorohydrin (VIII) as obtained in Example 26.

To a solution of sodium borohydride (6.34 g, 168 mmol) in tetrahydrofuran (100 ml) was added ethanol (100 ml) at about 25° C. and the mixture was stirred at that temperature for 2 hours. This mixture was added to a solution of L-[N-(t-butoxycarbonyl)phenylalanyl]methyl chloride (IV) (100 g, 335 mmol) in tetrahydrofuran (400 ml) and ethanol (400 ml) for about 40 minutes at an internal temperature of 10 and 15° C. This mixture was further stirred at an internal temperatue of about 10° C. for 30 minutes, and, then, concentrated sulfuric acid (3.23 g)/water (500 ml) was added at an internal temperature of 12 to 17° C. The mixtue was adjusted to pH about 6.3 with 30% sodium hydroxide, warmed to 50° C., and stirred for 30 minutes at that temperature. The mixture was cooled to about 10° C. and stirred at that temperautre for 1 hours. This mixture was filtered and the Filtrate was washed with water and ethanol in that order and dried to provide crystals of L-[N-(t-butoxycarbonyl)phenylalanyl]chlorohydrin (VIII) (59.0 g, 197 mmol, erythro/threo=98.4:1.6). The NMR and IR spectra of the product L-[N-(t-butoxycarbonyl)phenylalanyl] chlorohydrin (VIII) are presented in FIGS. 13 and 14, respectively.

$[\alpha]_D^{25}=-3.44$ (c=1.05, MeOH)

m.p.: 168.5 to 169.5° C.

Example 27

Production of L-[N-(t-butoxycarbonyl)phenylalanyl] epoxide (IX)

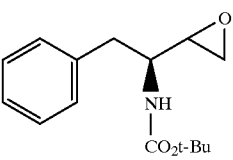

(IX)

Figure 15:
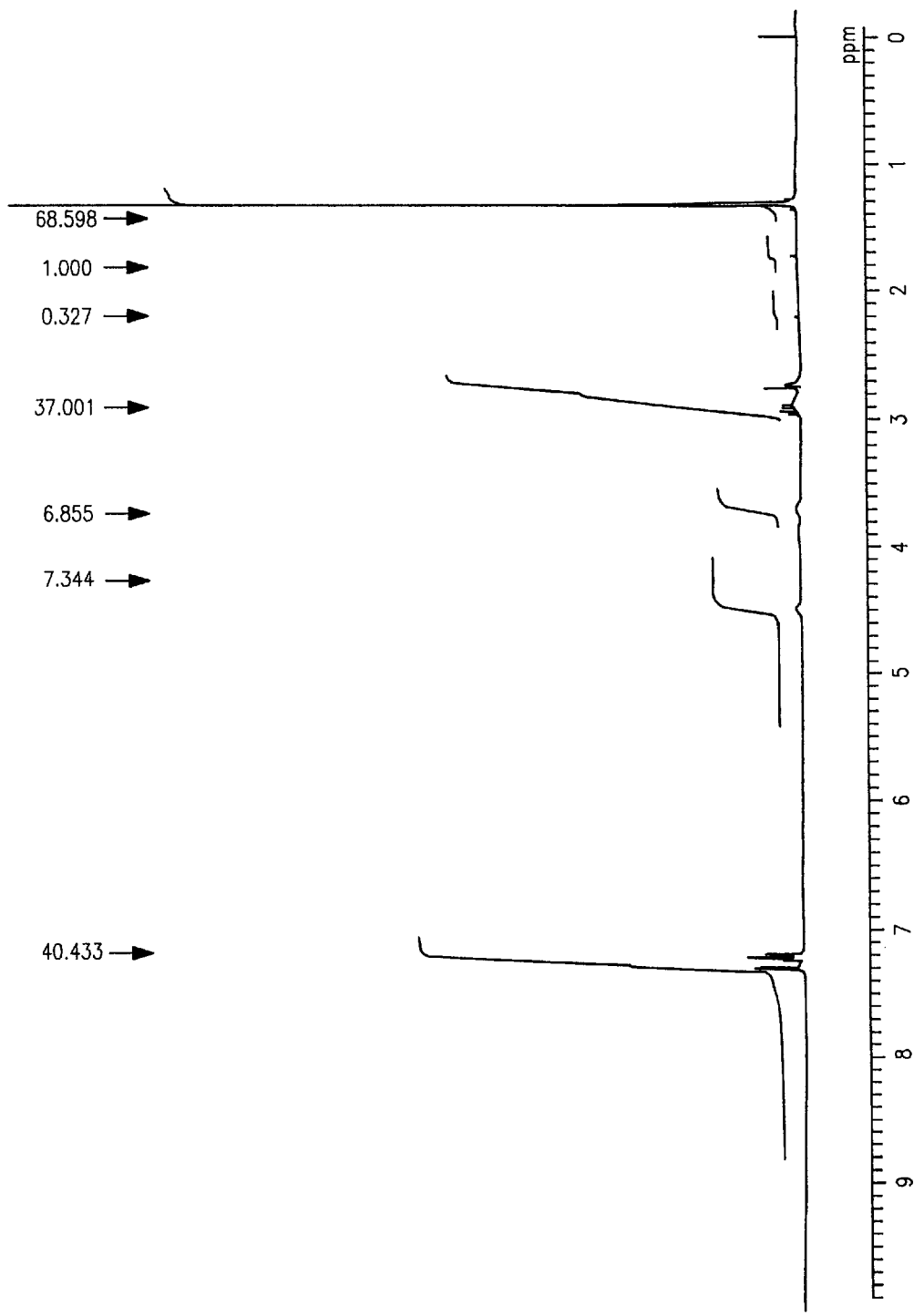
FIG. 15 shows an NMR chart of L-(N-t-butoxycarbonyl) phenylalanyl epoxide (IX) as obtained in Example 27.
Figure 16:
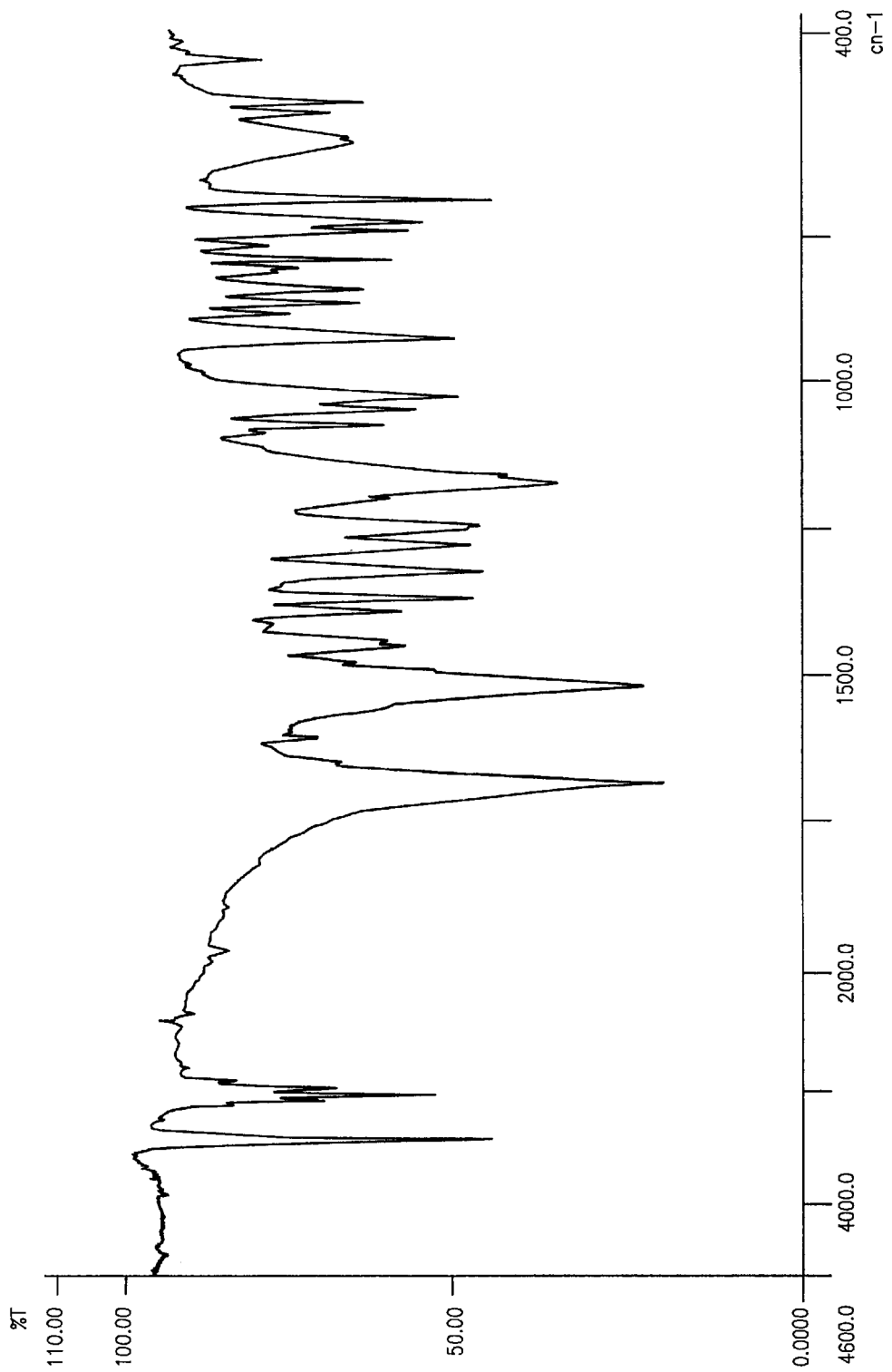
FIG. 16 shows an IR chart of L-(N-t-butoxycarbonyl) phenylalanyl epoxide (IX) as obtained in Example 27.

To a slurry of L-[N-(t-butoxycarbonyl)phenylalanyl] chlorohydrin (VIII) (17.0 g, 56.7 mmol) as obtained in Example 25 in 136 ml of acetone was added a solution of sodium hydroxide (3.4 g) in water (34 ml) for 15 minutes at about 25° C. The mixture was stirred at 25 to 40° C. for 1 hour, after which it was allowed to[ ]stand. After the acetone (upper) phase was warmed to 50° C. and 200 ml of water was added for 1 hour with constant stirring. Then, under stirring, the mixture was cooled to about 25° C. for 2 hours. After 1 hour of stirring at the same temperature, the reaction mixture was filtered and the precipitate was rinsed with acetone-water and dried to provide crystals of L-[N-(t-butoxycarbonyl)phenylalanyl] epoxide (IX) (13.73 g, 52.2 mmol, erythro/threo=99.6/0.4, yield 92.1%). The NMR and IR spectra of this L-[N-(t-butoxycarbonyl) .phenylalanyl] epoxide (IX) are presented in FIGS. 15 and 16, respectively.

$[\alpha]_D^{25}=-27.4$ (c=1.0, acetonitrile)

m.p.: 123.5 to 126.0° C.

Example 28

Production of L-[N-(benzyloxycarbonyl) phenylthioalanyl]methyl chloride (X)

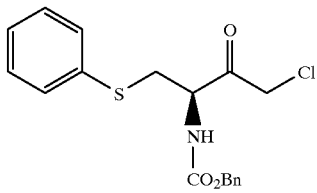

Figure 17:
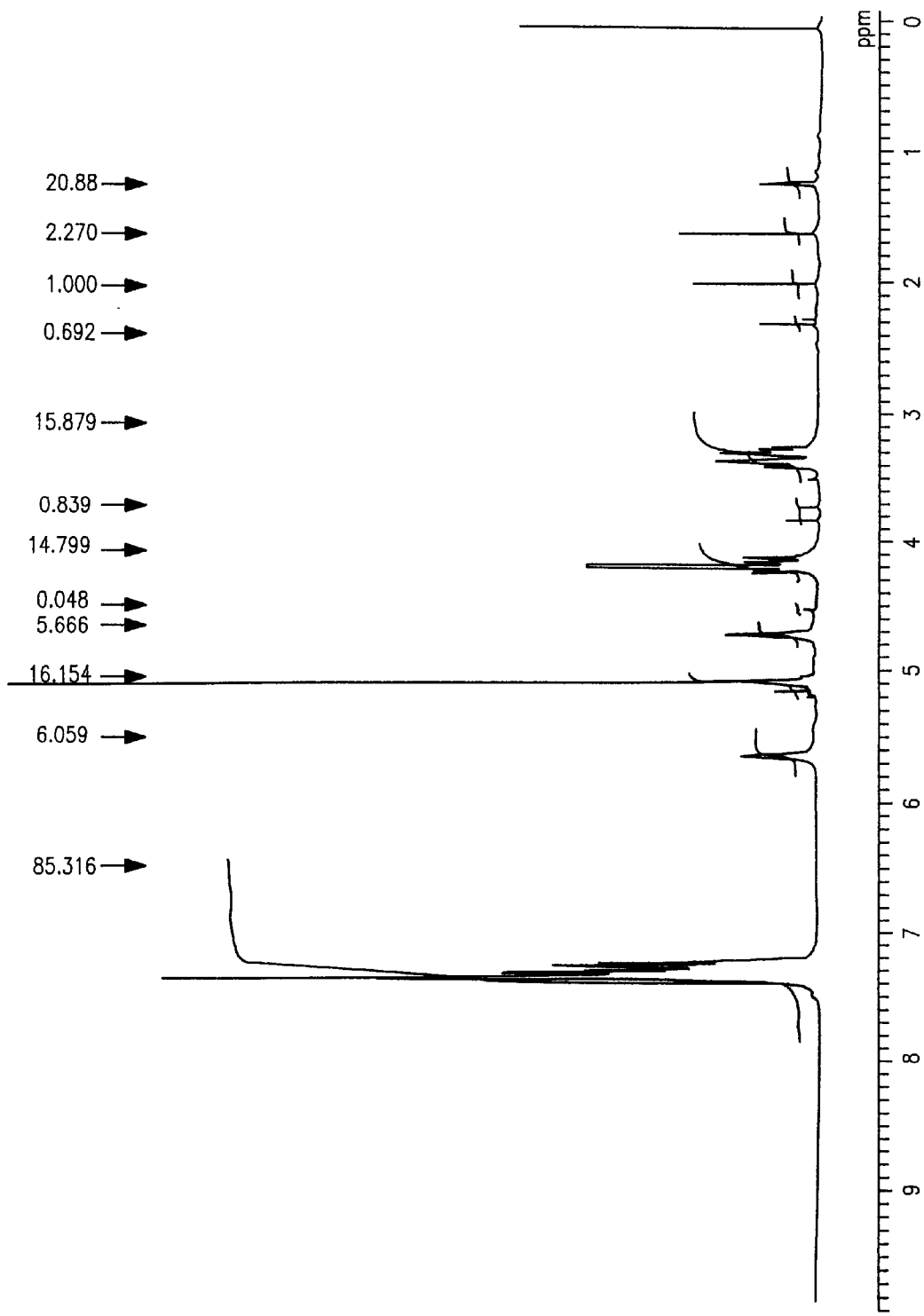
FIG. 17 shows an NMR chart of L-[N-(benzyloxycarbonyl)phenylthioalanyl]methyl chloride (X) as obtained in Example 28.
Figure 18:
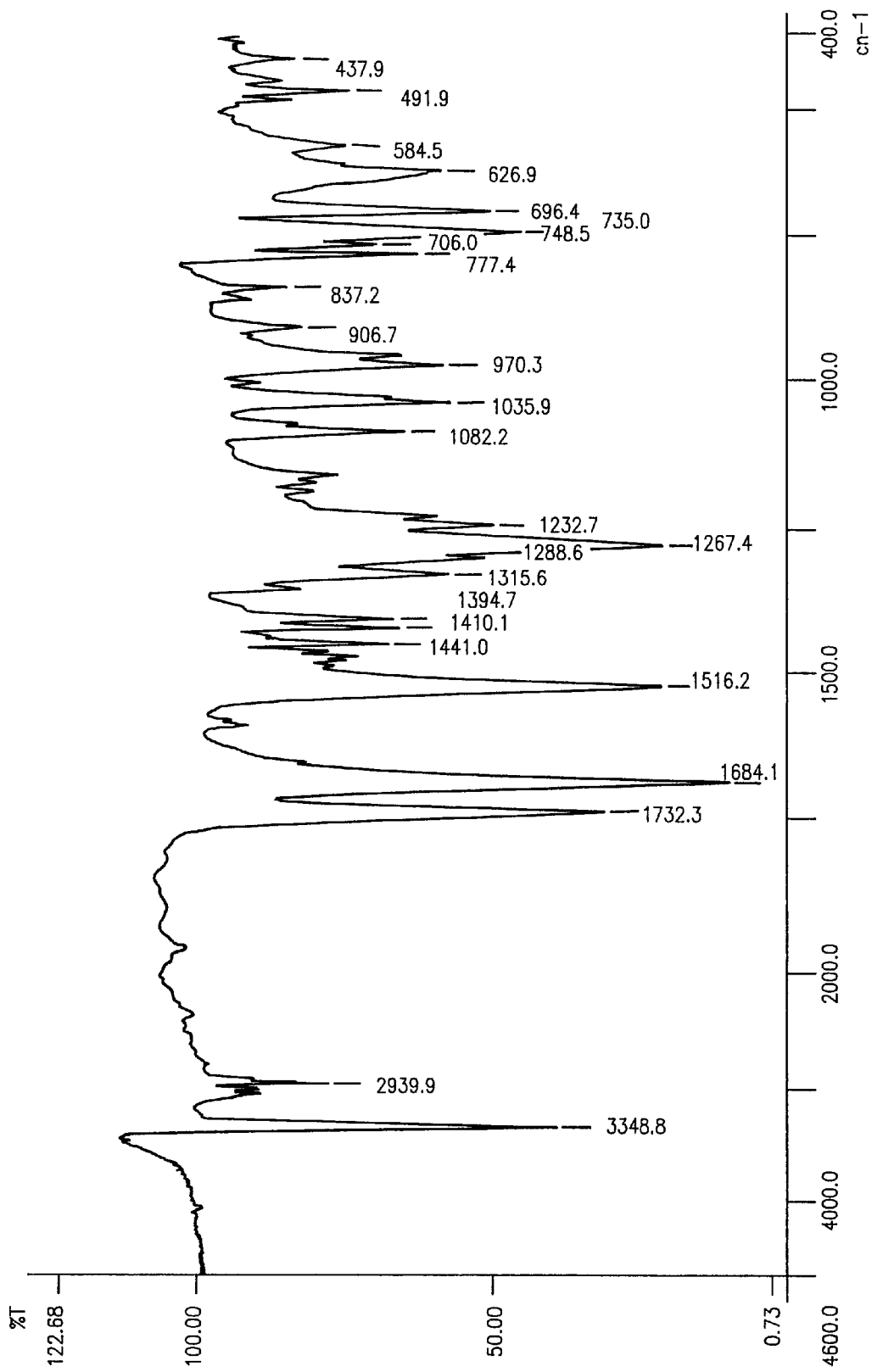
FIG. 18 shows an IR chart of L-[N-(benzyloxycarbonyl) phenylthioalanyl]methyl chloride (X) as obtained in Example 28.

Under the atomosphere of nitrogen gas, a solution of L-N-(benzyloxycarbonyl)phenylthioalanine methyl ester (2.0 g, 5.8 mmol), sodium monochloroacetate (1.35 g, 11.6 mmol) and magnesium chloride (1.105 g, 11.6 mmol) in THF (8 ml) was stirred at 25° C. for 1 hour (solution A). Separately, under the atomosphere of nitrogen gas, diisopropylamine (2.35 g, 23.2 mmol) was added to n-butylmagnesium chloride (2.0 mol/L THF, 11.6 ml, 23.2 mmol) for 30 minutes at room temperature and the mixture was stirred at 70° C. for 30 minutes (solution B). At an internal temperature of about 5° C., this solution B was added to the above solution A for about 15 minutes. After completion of this addition, the internal temperature was increased to 70° C. and the mixture was further stirred for 30 minutes. To this reaction mixture was added a solution consisting of sulfuric acid (2.28 g), water (20 ml) and ethyl acetate (30 ml) and the mixture was stirred for 30 minutes for hydrolysis. The organic phase was separated and washed with saturated aqueous NaHCO$_3$ solution (20 ml). The organic phase was then concentrated under reduced pressure to provide a yellow oil (2.249 g). This oil was purified using a silica gel column (hexane-ethyl acetate=5:1) to give crystals of L-[N-(benzyloxycarbonyl)phenylthioalanyl]methyl chloride (1.097 g, yield 52.0%). The NMR and IR spectra of this product L-[N-(benzyloxycarbonyl)phenylthioalanyl] methyl chloride (X) are presented in FIGS. 17 and 18, respectively.

$[\alpha]_D^{25}=-67.9$ m.p.: 37 to 88° C.

INDUSTRIAL APPLICABILITY

Since, in accordance with the present invention, α-halo ketones, α-halohydrins and epoxides can be produced effectively from carboxylic acid derivatives such as esters through the use of an α-haloacetic acid on an industrial scale as described above, optically active α-halo ketones, α-halohydrins and epoxides can be produced from the corresponding optically active N-protected phenylalanine esters So that the present invention can provide useful intermediates for the production of medicines.

We claim:

1. A process for producing an α-halo ketone of general formula (3)

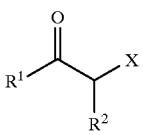

(3)

(wherein R$^1$ represents alkyl, aralkyl or aryl; R$^2$ represents hydrogen, alkyl, aralkyl or aryl; X represents halogen) which comprises reacting a carboxylic acid derivative of general formula (1)

R$^1$COA (1)

(wherein R$^1$ is as defined above; A represents a leaving group) with a metal enolate prepared from an α-haloacetic acid of the a general formula (2)

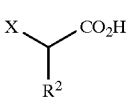

(2)

(wherein R$^2$ and X are as defined above) or an acceptable salt thereof and decarboxylating the reaction product in situ.

2. A process for producing an α-halo ketone of general formula (3)

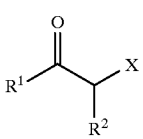

(3)

(wherein R$^1$ represents alkyl, aralkyl or aryl; R$^2$ represents hydrogen, alkyl, aralkyl or aryl; X represents halogen) which comprises reacting a carboxylic acid ester of general formula (4)

R$^1$CO$_2$R$^3$ (4)

(wherein R$^1$ and R$^3$ independently represent alkyl, aralkyl or aryl) with a metal enolate prepared from an α-haloacetic acid of general formula (2)

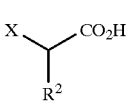

(2)

(wherein R$^2$ and X are as defined above) or an acceptable salt thereof and decarboxylating the reaction product in situ.

3. A process for producing an α-halo ketone as claimed in claim 1 wherein the metal enolate prepared from an α-haloacetic acid or an acceptable salt thereof is a magnesium enolate.

4. A process for producing an α-halo ketone as claimed in claim 3 wherein the magnesium enolate is prepared by reacting a magnesium amide of general formula (5)

 (5)

(wherein B and D independently represent alkyl, aralkyl, aryl or silyl or, taken together, represent cycloalkyl; Y represents

or halogen) with an α-haloacetic acid of general formula (2)

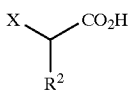 (2)

(wherein $R^2$ represents hydrogen, alkyl, aralkyl or aryl; X represents halogen) or an acceptable salt thereof.

5. A process for producing an α-halo ketone as claimed in claim 4 wherein the compound of general formula (5) is chloromagnesium diisopropylamide.

6. A process for producing an α-halo ketone as claimed in claim 3 wherein the magnesium enolate is prepared by reacting a Grignard reagent of general formula (6)

 (6)

(wherein $R^4$ represents alkyl, aralkyl, or aryl; Z represents halogen or $R^4$) with an α-haloacetic acid of general formula (2)

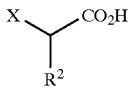 (2)

(wherein $R^2$ represents hydrogen, alkyl, aralkyl or aryl; X represents halogen) or an acceptable salt thereof.

7. A process for producing an α-halo ketone as claimed in claim 6 wherein the compound of general formula (6) is t-butylmagnesium chloride.

8. A process for producing an α-halo ketone as claimed in claim 6 wherein the reaction is conducted in the presence of an amine.

9. A process for producing an α-halo ketone as claimed in claim 8 wherein the amine is a secondary amine or a tertiary amine.

10. A process for producing an α-halo ketone as claimed in claim 1 wherein the acceptable salt of an α-haloacetic acid is a sodium salt of an α-haloacetic acid.

11. A process for producing an α-halo ketone as claimed in claim 1 wherein the acceptable salt of an α-haloacetic acid is a magnesium salt of an α-haloacetic acid of general formula (7)

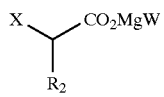 (7)

(wherein $R^2$ is as previously defined; W represents halogen or

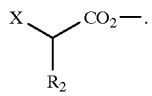

12. A process for producing an α-halo ketone as claimed in claim 11 wherein the magnesium salt of an α-haloacetic acid is one prepared from a sodium salt of an α-haloacetic acid and a magnesium halide or magnesium sulfate.

13. A process for producing an α-halo ketone as claimed in claim 11 wherein the magnesium salt of an α-haloacetic acid is one prepared from an α-haloacetic acid and metallic magnesium.

14. A process for producing an α-halo ketone as claimed in claim 1 wherein the α-haloacetic acid is a monochloroacetic acid.

15. A process for producing an α-halo ketone as claimed in claim 1 wherein the acceptable salt of an α-haloacetic acid is an ammonium salt of the α-haloacetic acid.

16. A process for producing an α-halo ketone as claimed in claim 1 wherein the metal enolate formed from an α-haloacetic acid or an acceptable salt thereof is a lithium dianion of a monochloroacetic acid.

17. A process for producing an α-halo ketone as claimed in claim 1 wherein the metal enolate formed from an α-haloacetic acid or an acceptable salt thereof is a magnesium dianion of a monochloroacetic acid.

18. A process for producing an α-halo ketone of general formula (9)

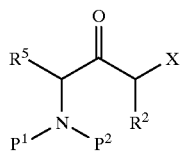 (9)

(wherein $R^2$ represents hydrogen, alkyl, aralkyl or aryl; $R^5$ represents hydrogen, alkyl, aralkyl or aryl; $P^1$ and $P^2$ independently represent hydrogen or amino protecting group or, taken together, represent phthaloyl; X represents halogen) which comprises reacting an amino acid derivative of general formula (8)

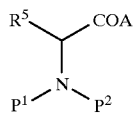 (8)

(wherein $R^5$, $P^1$ and $P^2$ are as defined above; A represents a leaving group) with a metal enolate prepared from an α-haloacetic acid of general formula (2)

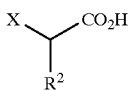

(wherein $R^2$ and X are as defined above) or an acceptable salt thereof and decarboxylating the reaction product in situ.

19. A process for producing an α-halo ketone of general formula (9)

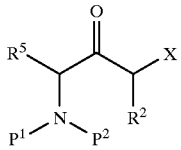

(wherein $R^2$ represents hydrogen, alkyl, aralkyl or aryl; $R^5$ represents hydrogen, alkyl, aralkyl or aryl; $P^1$ and $P^2$ independently represent hydrogen or amino protecting group or, taken together, represent phthaloyl; X represents halogen) which comprises reacting an amino acid ester derivative of general formula (10)

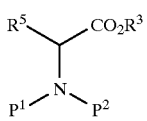

(wherein $R^3$ represents alkyl, aralkyl or aryl; $R^5$, $P^1$ and $P^2$ are as defined above) with a metal enolate prepared from an α-haloacetic acid of general formula (2)

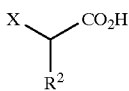

(wherein $R^2$ and X are as defined above) or an acceptable salt thereof and decarboxylating the reaction product in situ.

20. A process for producing an α-halo ketone as claimed in claim 19 wherein the amino acid ester derivative is an optically active L-amino acid ester derivative or an optically active D-amino acid ester derivative.

21. A process for producing an α-halo ketone as claimed in claim 20 wherein the amino acid ester derivative is an optically active L-phenylalanine ester derivative or an optically active D-phenylalanine ester derivative.

22. A process for producing an α-halo ketone as claimed in claim 21 wherein the optically active L-phenylalanine ester derivative or optically active D-phenylalanine ester derivative is a derivative selected from the group consisting of a t-butoxycarbonyl-protected L-phenylalanine ester, benzyloxycarbonyl-protected L-phenylalanine ester, methoxycarbonyl-protected L-phenylalanine ester, and ethoxycarbonyl-protected L-phenylalanine ester.

23. A process for producing an α-halo ketone as claimed in claim 18 wherein the metal enolate prepared from an α-haloacetic acid or an acceptable salt thereof is a magnesium enolate.

24. A process for producing an α-halo ketone as claimed in claim 23 wherein the magnesium enolate is prepared by reacting a magnesium amide of general formula (5)

(wherein B and D independently represent alkyl, aralkyl, aryl or silyl or, taken together, represent cycloalkyl; Y represents

or halogen) with an α-haloacetic acid of the general formula (2)

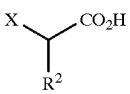

(wherein $R^2$ represents hydrogen, alkyl, aralkyl or aryl; X represents halogen) or an acceptable salt thereof.

25. A process for producing an α-halo ketone as claimed in claim 24 wherein the compound of general formula (5) is chloromagnesium diisopropylamide.

26. A process for producing an α-halo ketone as claimed in claim 23 wherein the magnesium enolate is prepared by reacting a compound Grignard reagent of general formula (6)

$$R^4MgZ \quad (6)$$

(wherein $R^4$ represents alkyl, aralkyl, or aryl; Z represents halogen or $R^4$) with an α-haloacetic acid of general formula (2)

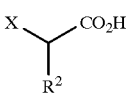

(wherein $R^2$ represents hydrogen, alkyl, aralkyl or aryl; X represents halogen) or an acceptable salt thereof.

27. A process for producing an α-halo ketone as claimed in claim 26 wherein the compound of general formula (6) is t-butylmagnesium chloride.

28. A process for producing an α-halo ketone as claimed in claim 26 or 27 wherein the reaction is conducted in the presence of an amine.

29. A process for producing an α-halo ketone as claimed in claim 28 wherein the amine is a secondary amine or a tertiary amine.

30. A process for producing an α-halo ketone as claimed in claim 18 wherein the acceptable salt of an α-haloacetic acid is sodium monochloroacetate.

31. A process for producing an α-halo ketone as claimed in claim 18 wherein the acceptable salt of an α-haloacetic acid is a magnesium salt of an α-haloacetic acid of general formula (7)

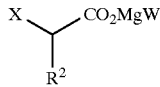
(7)

(wherein R² is as previously defined; W represents halogen or

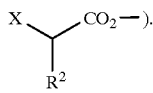
).

32. A process for producing an α-halo ketone as claimed in claim 31 wherein the magnesium salt of an α-haloacetic acid is one prepared from a sodium salt of an α-haloacetic acid and either a magnesium halide or magnesium sulfate.

33. A process for producing an α-halo ketone as claimed in claim 31 wherein the magnesium salt of an α-haloacetic acid is one prepared from an α-haloacetic acid and metallic magnesium.

34. A process for producing an α-halo ketone as claimed in claim 18 wherein the α-haloacetic acid is monochloroacetic acid.

35. A process for producing an α-halo ketone as claimed in claim 18 wherein the acceptable salt of an α-haloacetic acid is an ammonium salt of an α-haloacetic acid.

36. A process for producing an α-halo ketone as claimed in claim 18 wherein the metal enolate formed from an α-haloacetic acid or an acceptable salt thereof is a magnesium dianion of a monochloroacetic acid.

37. A process for producing an α-halo ketone as claimed in claim 18 wherein the metal enolate formed from an α-haloacetic acid or an acceptable salt thereof is a lithium dianion of a monochloroacetic acid.

38. A process for producing an α-halohydrin of general formula (11)

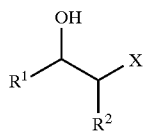
(11)

(wherein R¹ and R² independently represent hydrogen, alkyl, aralkyl, or aryl; X represents halogen) which comprises producing an α-halo ketone of general formula (3)

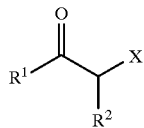
(3)

(wherein R¹, R² and X are as defined above) in accordance with the process according to claim 1 and reducing said α-halo ketone.

39. A process for producing an α-halohydrin of general formula (12)

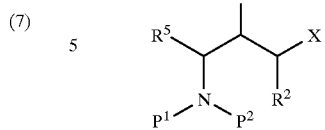
(12)

(wherein R² and R⁵ independently represent hydrogen, alkyl, aralkyl, or aryl; P¹ and P² independently represent hydrogen or amino protecting group or, taken together, represent phthaloyl; X represents halogen) which comprises producing an α-halo ketone of general formula (9)

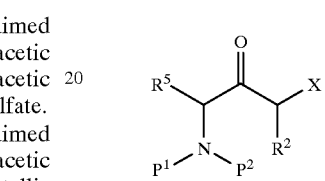
(9)

(wherein R², R⁵, P¹, P² and X are as defined above) in accordance with the process according to claim 18 and reducing said α-halo ketone.

40. A process for producing an α-halohydrin as claimed in claim 39 wherein the amino acid derivative is an optically active L-amino acid ester derivative or an optically active D-amino acid ester derivative.

41. A process for producing an α-halohydrin as claimed in claim 40 wherein the optically active L-amino acid ester derivative or optically active D-amino acid ester derivative is an optically active L-phenylalanine ester derivative or an optically active D-phenylalanine ester derivative.

42. A process for producing an α-halohydrin as claimed in claim 41 wherein the amino acid derivative is a derivative selected from the group consisting of a t-butoxycarbonyl-protected L-phenylalanine ester, benzyloxycarbonyl-protected L-phenylalanine ester, methoxycarbonyl-protected L-phenylalanine ester, ethoxycarbonyl-protected L-phenylalanine ester, t-butoxycarbonyl-protected D-phenylalanine ester, benzyloxycarbonyl-protected D-phenylalanine ester, methoxycarbonyl-protected D-phenylalanine ester and ethoxycarbonyl-protected D-phenylalanine ester.

43. A process for producing an epoxide of general formula (13)

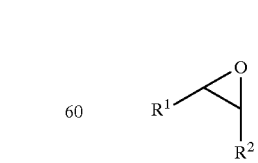
(13)

(wherein R¹, R² independently represent hydrogen, alkyl, aralkyl, or aryl) which compsises producing an α-halohydrin of general formula (11)

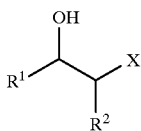

(11)

(wherein $R^1$ and $R^2$ are as defined above; X represents halogen) in accordance with the process according to claim 38 and treating the α-halohydrin with a base.

44. A process for producing an epoxide of general formula (14)

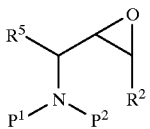

(14)

(wherein $R^2$ and $R^5$ independently represent hydrogen, alkyl, aralkyl, or aryl; $P^1$ and $P^2$ independently represent hydrogen or an amino-protecting group or, taken together, represent phthaloyl) which comprises producing an α-halohydrin of general formula (12)

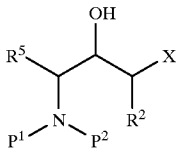

(12)

(wherein $R^2$, $R^5$, $P^1$ and $P^2$ are as defined above; X represents halogen) in accordance with the process according to claim 39 and treating said α-halohydrin with a base.

45. A process for producing an epoxide as claimed in claim 44 wherein the amino acid derivative is an optically active L-amino acid ester derivative or an optically active D-amino acid ester derivative.

46. A process for producing an epoxide as claimed in claim 45 wherein the optically active L-amino acid ester derivative or optically active D-amino acid ester derivative is an optically active L-phenylalanine ester derivative or an optically active D-phenylalanine ester derivative.

47. A process for producing an epoxide as claimed in claim 45 wherein the amino acid derivative is a derivative selected from the group consisting of a t-butoxycarbonyl-protected L-phenylalanine ester, benzyloxycarbonyl-protected L-phenylalanine ester, methoxycarbonyl-protected L-phenylalanine ester, ethoxycarbonyl-protected L-phenylalanine ester, t-butoxycarbonyl-protected D-phenylalanine ester, benzyloxycarbonyl-protected D-phenylalanine ester, methoxycarbonyl-protected D-phenylalanine ester and ethoxycarbonyl-protected D-phenylalanine ester.

48. A process for producing an α-halo ketone as claimed in claim 20 wherein the optically active D-amino acid ester derivative or the optically active L-amino acid ester derivative is a D-phenylthioalanine ester derivative or L-phenylthioalanine ester derivative.

49. A process for producing an α-halo ketone as claimed in claim 48 wherein the D-phenylthioalanine ester derivative or L-phenylthioalanine ester derivative is a benzyloxycarbonyl-protected D-phenylthioalanine ester or benzyloxycarbonyl-protected L-phenylthioalanine ester.

50. A process for producing an α-halohydrin as claimed in claim 40 wherein the optically active D-amino acid ester compound or the optically active L-amino acid ester compound is a D-phenylthioalanine ester compound or L-phenylthioalanine ester compound.

51. A process for producing an α-halohydrin as claimed in claim 50 wherein the D-phenylthioalanine ester compound or L-phenylthioalanine ester compound is a benzyloxycarbonyl-protected D-phenylthioalanine ester or benzyloxycarbonyl-protected L-phenylthioalanine ester.

52. A process for producing an epoxide as claimed in claim 45 wherein the optically active D-amino acid ester compound or the optically active L-amino acid ester compound is a D-phenylthioalanine ester compound or L-phenylthioalanine ester.

53. A process for producing an epoxide as claimed in claim 52 wherein the D-phenylthioalanine ester compound or L-phenylthioalanine ester compound is a benzyloxycarbonyl-protected D-phenylthioalanine ester or benzyloxycarbonyl-protected L-phenylthioalanine ester.

* * * * *